(12) United States Patent
Gardner, Jr. et al.

(10) Patent No.: US 7,738,095 B2
(45) Date of Patent: *Jun. 15, 2010

(54) METHOD AND APPARATUS FOR COMPACT SPECTROMETER FOR DETECTING HAZARDOUS AGENTS

(75) Inventors: Charles W. Gardner, Jr., Gibsonia, PA (US); John S. Maier, Pittsburgh, PA (US); Matthew P. Nelson, Harrison City, PA (US); Robert C. Schweitzer, Pittsburgh, PA (US); Patrick J. Treado, Pittsburgh, PA (US); G. Steven Vanni, Pittsburgh, PA (US); Julianne Wolfe, Pittsburgh, PA (US); Joseph E. Demuth, Pittsburgh, PA (US); Jason H. Neiss, Pittsburgh, PA (US); Chenhui Wang, Stow, OH (US)

(73) Assignee: ChemImage Corporation, Pittsburgh, PA (US)

( * ) Notice: Subject to any disclaimer, the term of this patent is extended or adjusted under 35 U.S.C. 154(b) by 864 days.

This patent is subject to a terminal disclaimer.

(21) Appl. No.: 11/366,532

(22) Filed: Mar. 3, 2006

(65) Prior Publication Data

US 2006/0203238 A1 Sep. 14, 2006

Related U.S. Application Data

(63) Continuation-in-part of application No. 11/366,600, filed on Mar. 3, 2006, and a continuation-in-part of application No. 11/366,531, filed on Mar. 3, 2006, and a continuation-in-part of application No. 11/000,683, filed on Nov. 30, 2004, and a continuation-in-part of application No. 10/893,331, filed on Jul. 19, 2004, and a continuation-in-part of application No. 10/893,230, filed on Jul. 19, 2004, and a continuation-in-part of application No. 10/893,339, filed on Jul. 19, 2004, and a continuation-in-part of application No. 10/893,332, filed on Jul. 19, 2004, now Pat. No. 7,012,695.

(60) Provisional application No. 60/772,624, filed on Feb. 13, 2006, provisional application No. 60/591,132, filed on Jul. 26, 2004, provisional application No. 60/584,718, filed on Jun. 30, 2004, provisional application No. 60/488,246, filed on Jul. 18, 2003.

(51) Int. Cl.
*G01J 3/44* (2006.01)
*G01N 21/65* (2006.01)

(52) U.S. Cl. ..................................... 356/301; 356/300

(58) Field of Classification Search ................. 356/300, 356/301

See application file for complete search history.

(56) References Cited

U.S. PATENT DOCUMENTS

| 3,984,190 A | 10/1976 | Barrett et al. |
| 4,195,931 A | 4/1980 | Hara |

(Continued)

FOREIGN PATENT DOCUMENTS

| EP | 1314972 A1 | 5/2003 |
| WO | 99/27140 A1 | 6/1999 |
| WO | 02/095376 A2 | 11/2002 |
| WO | 2005/060380 A2 | 7/2005 |

OTHER PUBLICATIONS

Conti, S., et al., "Traces of Polymethylsiloxane in case histories of rape: technique for detection," Elsvier Science Ireland Ltd, Forensic Science International, Jan. 1995, pp. 121-128.

(Continued)

*Primary Examiner*—L. G Lauchman
(74) *Attorney, Agent, or Firm*—Duane Morris LLP

(57) ABSTRACT

The disclosure relates to a portable system for obtaining a spatially accurate wavelength-resolved image of a sample having a first and a second spatial dimension that can be used for the detection of hazardous agents by irradiating a sample with light, forming an image of all or part of the sample using Raman shifted light from the sample, and analyzing the Raman shifted light for patterns characteristic of one or more hazardous agents.

32 Claims, 21 Drawing Sheets

U.S. PATENT DOCUMENTS

| | | | |
|---|---|---|---|
| 4,200,801 A | 4/1980 | Schuresko | |
| 4,553,816 A | 11/1985 | Durand et al. | |
| 4,660,151 A | 4/1987 | Chipman et al. | |
| 4,701,838 A | 10/1987 | Swinkels et al. | |
| 4,766,551 A | 8/1988 | Begley | |
| 4,885,697 A | 12/1989 | Hubner | |
| 5,072,338 A | 12/1991 | Hug et al. | |
| 5,121,337 A | 6/1992 | Brown | |
| 5,121,338 A | 6/1992 | Lodder | |
| 5,124,932 A | 6/1992 | Lodder | |
| 5,311,445 A | 5/1994 | White | |
| 5,324,567 A | 6/1994 | Bratchley et al. | |
| 5,347,378 A | 9/1994 | Handschy et al. | |
| 5,357,340 A | 10/1994 | Zochbauer | |
| 5,481,476 A | 1/1996 | Windig | |
| 5,606,164 A | 2/1997 | Price et al. | |
| 5,610,836 A | 3/1997 | Alsmeyer et al. | |
| 5,710,713 A | 1/1998 | Wright et al. | |
| 5,751,415 A | 5/1998 | Smith et al. | |
| 5,801,828 A | 9/1998 | Collins | |
| 5,822,219 A | 10/1998 | Chen et al. | |
| 5,866,430 A * | 2/1999 | Grow | 506/6 |
| 6,002,476 A | 12/1999 | Treado | |
| 6,008,888 A | 12/1999 | Nottke et al. | |
| 6,239,904 B1 | 5/2001 | Serfling et al. | |
| 6,485,981 B1 | 11/2002 | Fernandez | |
| 6,549,861 B1 | 4/2003 | Mark et al. | |
| 6,584,413 B1 | 6/2003 | Keenan et al. | |
| 6,614,532 B1 * | 9/2003 | Power et al. | 356/432 |
| 6,621,614 B1 | 9/2003 | Zhang | |
| 6,631,001 B2 | 10/2003 | Kuiseko | |
| 6,833,957 B2 | 12/2004 | Sato | |
| 6,836,366 B1 | 12/2004 | Flanders et al. | |
| 6,897,951 B2 * | 5/2005 | Womble et al. | 356/301 |
| 6,970,246 B2 | 11/2005 | Hansen et al. | |
| 6,992,819 B2 * | 1/2006 | Vodyanoy | 359/368 |
| 7,072,770 B1 | 7/2006 | Schweitzer et al. | |

OTHER PUBLICATIONS

Lee, G.S.H., et al., "A Methodology Based on NMR Spectroscopy for the Forensic Analysis of Condoms," St. Andrews Centre for Advanced Materials, pp. 808-821.

Maynard, P., et al., "A protocol for the forensic analysis of condom and personal lubricants found in sexual assault cases," Forensic Science International, 124 (2001), pp. 140-156.

Stoilovic, M., et al., "The Application of Light in Forensic Science & A Modern Approach to Fingerprint Detection and Enhancement," Australian Federal Police, AFP Workshop Manual, Oct. 2000.

Roux, C., et al., "Evaluation of 1,2-Indanedione and 5,6-Dimethoxy-1,2-Indanedione for the Detection of Latent Fingerprints on Porous Surfaces," Journal of Forensic Sciences, vol. 45(4), 2000, pp. 761-769.

Roux, C., et al., "A study to investigate the evidential value of blue and black ballpoint pen inks in Australia," Forensic Science International, 101 (1999), pp. 167-176.

Mazzella, W.D., et al., "Classification and Identification of Photocopying Toners by Diffuse Reflectance Infrared Fourier Transform Spectroscopy (DRIFTS): I. Preliminary Results," Journal of Forensic Sciences, JFSCA, vol. 36, No. 2, Mar. 1991, pp. 449-465.

Mazzella, W.D., et al., "Classification and Identification of Photocopying Toners by Diffuse Reflectance Infrared Fourier Transform Spectroscopy (DRIFTS): II. Final Report," Journal of Forensic Sciences, JFSCA, vol. 36, No. 3, May 1991, pp. 820-837.

Brunelle, R.L., "Questioned Document Examination," Bureau of Alcohol, Tobacco, and Firearms, U.S. Treasury Department, 1982.

Robertson, J., et al., "The Persistence of Textile Fibres Transferred During Simulated Contacts," Journal of Forensic Sciences, vol. 22, No. 4, Oct. 1982, p. 353-360.

Gaudette, B.D., "The Forensic Aspects of Textile Fiber Examination," Central Forensic Laboratory, Royal Canadian Mounted Police.

Pounds, C.A., et al., "The Transfer of Fibres between Clothing Materials During Simulated Contacts and their Persistence During Wear: Part I—Fibre Transference," Journal of Forensic Sciences, vol. 15, 1975, pp. 17-27.

Pounds, C.A., et al., "The Transfer of Fibres between Clothing Materials During Simulated Contacts and their Persistence During Wear: Part II—Fibre Persistence," Journal of Forensic Sciences, vol. 15, 1975, pp. 29-37.

Maynard, P., et al., "Adhesive Tape Analysis: Establishing the Evidential Value of Specific Techniques," Journal of Forensic Sciences, vol. 46(2), 2001, pp. 280-287.

Caetano, M.R., et al., "Evaluation of the importance of non-linear spectral mixing in coniferous forests," EUROPTO Conference on Remote Sensing for Agriculture, Ecosystems, and Hydrology, Barcelona, Spain, Sep. 1998.

Rasmussen, G.T., et al., "Library Retrieval of Infrared Spectra Based on Detailed Intensity Information," Applied Spectroscopy, vol. 33, No. 4, 1979.

Guilment, J., et al., "Infrared Chemical Micro-Imaging Assisted by Interactive Self-Modeling Multivariate Analysis," Applied Spectroscopy, vol. 48, No. 3, 1994.

Engman, E.T., "Remote Sensing for Agriculture, Ecosystems, and Hydrology," Proceedings of SPIE EUROPTO Series, vol. 3499, Sep. 22-24, 1998.

Press, W.H., et al., Numerical Recipes in C, The Art of Scientific Computing, 2nd ed., Cambridge, NY: Cambridge University Press, 1992.

Malinowski, E.R., Factor Analysis in Chemistry, 2nd ed., New York, NY: John Wiley & Sons, Inc., 1991.

* cited by examiner

Fig. 16: FAST Spatial Mapping

METHOD AND APPARATUS FOR COMPACT SPECTROMETER FOR DETECTING HAZARDOUS AGENTS

RELATED APPLICATIONS

The instant application is a continuation-in-part of U.S. application Ser. No. 10/893,332, filed Jul. 19, 2004, now U.S. Pat. No. 7,012,695, which claims filing date priority to U.S. Provisional Application Ser. No. 60/488,246 filed Jul. 18, 2003. The instant application is also a continuation-in-part of, and therefore claims filing date priority to, U.S. application Ser. Nos. 10/893,339 ("Method and Apparatus for Compact Dispersive Imaging Spectrometer"), 10/893,230 ("Method and Apparatus for Multiwavelength Imaging Spectrometer") and 10/893,331 ("Method and Apparatus for Compact Birefringent Interference Imaging Spectrometer") which were all filed on Jul. 19, 2004. Also, the instant application is a continuation-in-part of, and therefore claims filing date priority to, U.S. application Ser. No. 11/000,683 Nov. 30, 2004 ("Multipoint Method for Identifying Hazardous Agents"), which claims filing date priority to U.S. Provisional Application Nos. 60/584,718 filed Jun. 30, 2004 and 60/591,132 filed Jul. 26, 2004. Further, the instant application claims filing date priority to, U.S. Provisional Application No. 60/772,624 filed Feb. 13, 2006. Additionally, the instant application is a continuation-in-part of, and therefore claims priority to, U.S. application Ser. No. 11/366,660 filed Mar. 3, 2006 ("Method and Apparatus for Compact Spectrometer for Multipoint Sampling of an Object"), and U.S. application Ser. No. 11/366,531 filed Mar. 3, 2006 ("Method and Apparatus for Compact Spectrometer with Fiber Array Spectral Translator"), both of which are filed concurrently herewith.

BACKGROUND

Spectroscopic imaging combines digital imaging and molecular spectroscopy techniques, which can include Raman scattering, fluorescence, photoluminescence, ultraviolet, visible and infrared absorption spectroscopes. When applied to the chemical analysis of materials, spectroscopic imaging is commonly referred to as chemical imaging. Instruments for performing spectroscopic (i.e. chemical) imaging typically comprise image gathering optics, focal plane array imaging detectors and imaging spectrometers.

In general, the sample size determines the choice of image gathering optic. For example, a microscope is typically employed for the analysis of sub micron to millimeter spatial dimension samples. For larger objects, in the range of millimeter to meter dimensions, macro lens optics are appropriate. For samples located within relatively inaccessible environments, flexible fiberscopes or rigid borescopes can be employed. For very large scale objects, such as planetary objects, telescopes are appropriate image gathering optics.

For detection of images formed by the various optical systems, two-dimensional, imaging focal plane array (FPA) detectors are typically employed. The choice of FPA detector is governed by the spectroscopic technique employed to characterize the sample of interest. For example, silicon (Si) charge-coupled device (CCD) detectors or CMOS detectors are typically employed with visible wavelength fluorescence and Raman spectroscopic imaging systems, while indium gallium arsenide (InGaAs) FPA detectors are typically employed with near-infrared spectroscopic imaging systems.

A variety of imaging spectrometers have been devised for spectroscopic imaging systems. Examples include, without limitation, grating spectrometers, filter wheels, Sagnac interferometers, Michelson interferometers, Twynam-Green interferometers, Mach-Zehnder interferometers, and tunable filters such as acousto-optic tunable filters (AOTFs) and liquid crystal tunable filters (LCTFs). Preferably, liquid crystal imaging spectrometer technology is used for wavelength selection. A liquid crystal imaging spectrometer may be one or a hybrid of the following types: Lyot liquid crystal tunable filter ("LCTF"), Evans Split-Element LCTF, Solc LCTF, Ferroelectric LCTF, Fabry Perot LCTF. Additionally, fixed bandpass and bandreject filters comprised of dielectric, rugate, holographic, color absorption, acousto-optic or polarization types may also be used, either alone or in combination with one of the above liquid crystal spectrometers.

A number of imaging spectrometers, including acousto-optical tunable filters (AOTF) and liquid crystal tunable filters (LCTF) are polarization sensitive, passing one linear polarization and rejecting the orthogonal linear polarization. AOTFs are solid-state birefringent crystals that provide an electronically tunable spectral notch pass band in response to an applied acoustic field. LCTFs also provide a notch pass band that can be controlled by incorporating liquid crystal retarders within a birefringent interference filter such as a Lyot filter. Conventional systems are generally bulky and not portable. A handheld chemical imaging sensor capable of performing instant chemical analysis would represent progress in size, weight and cost reduction. Accordingly, there is a need for a handheld, portable and more efficient tunable filter.

SUMMARY OF THE DISCLOSURE

In one embodiment, the disclosure relates to a portable system for obtaining a spatially accurate wavelength-resolved image of a sample having a first and a second spatial dimension that can be used for the detection of hazardous agents by irradiating a sample with light, forming an image of all or part of the sample using Raman shifted light from the sample, and analyzing the Raman shifted light for patterns characteristic of one or more hazardous agents.

DETAILED DESCRIPTION

Figure 1:
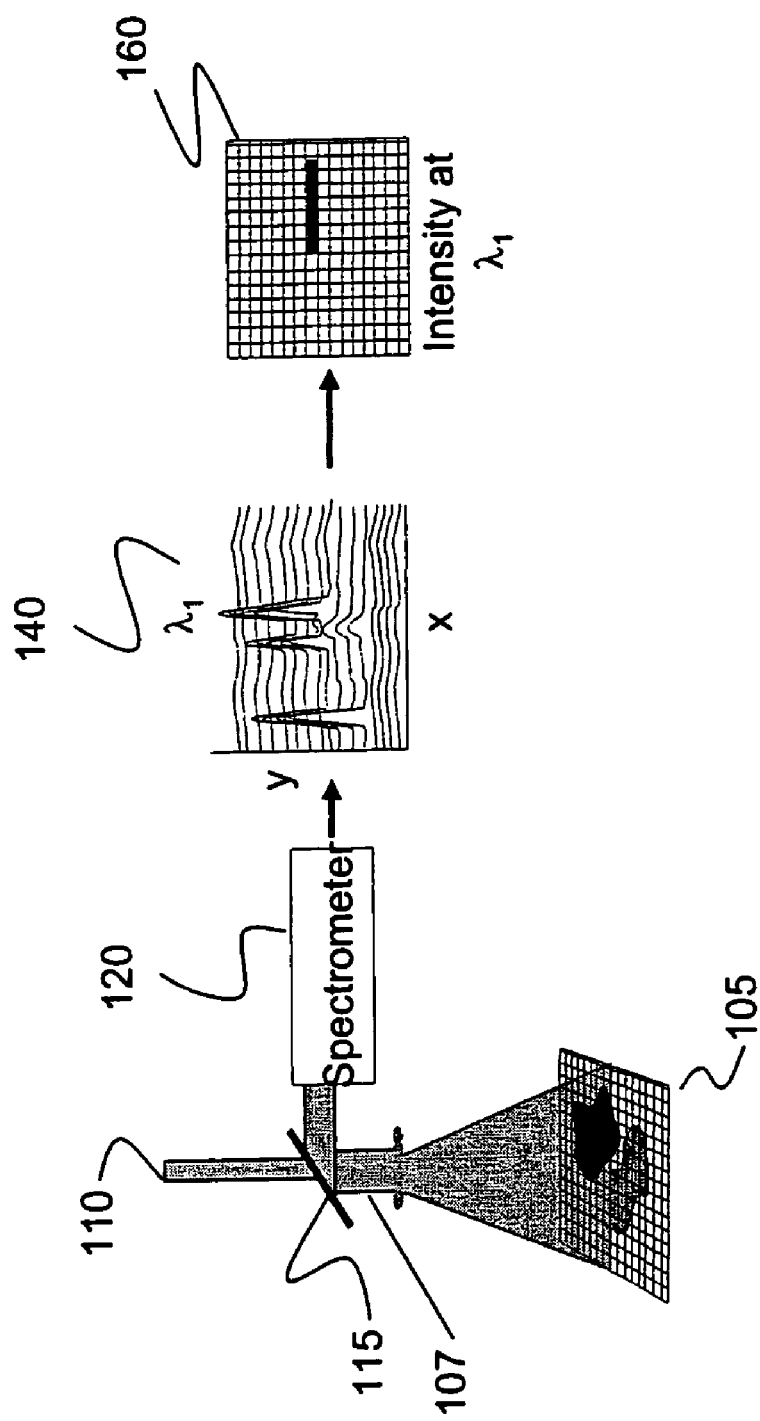
FIG. 1 is a schematic representation of a conventional line scan Raman imaging system.

FIG. 1 is a schematic representation of one type of conventional line scan Raman imaging system, in particular a dispersive scan Raman imaging system employing a "pushbroom" scanning arrangement. A sample 105 is illuminated from a source 110, and light energy is reflectively back scattered from the sample and collected at optics 115. The image of the sample is accumulated from successive images at adjacent parallel lines in the image. The image of the sample is obtained for each such line and also at each of a plurality of specific wavelengths in the spectrum. Thus, a line or one-dimensional set of light amplitude values is sampled at a given location $X_1, Y_1 \ldots Y_n$. The light is filtered for specific wavelengths using a spectrometer 120 that functions as a variable wavelength bandpass filter. By advancing from line to line in a "pushbroom" sequence, the successive amplitude values shown graphically at plot 140 are converted to intensity pixel values in an array 160 for a given wavelength $\lambda_1$. By sampling at different wavelengths, a separate substantially monochromatic image 160 is collected for each wavelength value $\lambda_1$ to $\lambda_n$. An object of this technique conventionally is to produce a set of monochromatic images that can be compared to one another to assist in identifying features in the image that may be characterized by contrast in their intensity versus adjacent features and other wavelengths.

The source 110 may be a laser, a fluorescent source or another source. Reflectively scattered photons are received by optical objective 107 and directed to spectrometer 120 via optical device 115. The particular arrangements for collecting the image of a line of pixels can involve focusing an image on a linear photosensor array of CCDs or the like, or scanning and sampling with one photosensor. The spectrometer 120 needs to be tunable in some way to selectively pass one wavelength bandpass at a time. It is possible in different configurations to use gratings or prisms or birefringent crystal arrangements for wavelength selection. In tuning from on wavelength to another and in advancing from one line to another (in whatever order), it may take a substantial time to collect the amplitude values for each pixel position and each wavelength.

Figure 2:
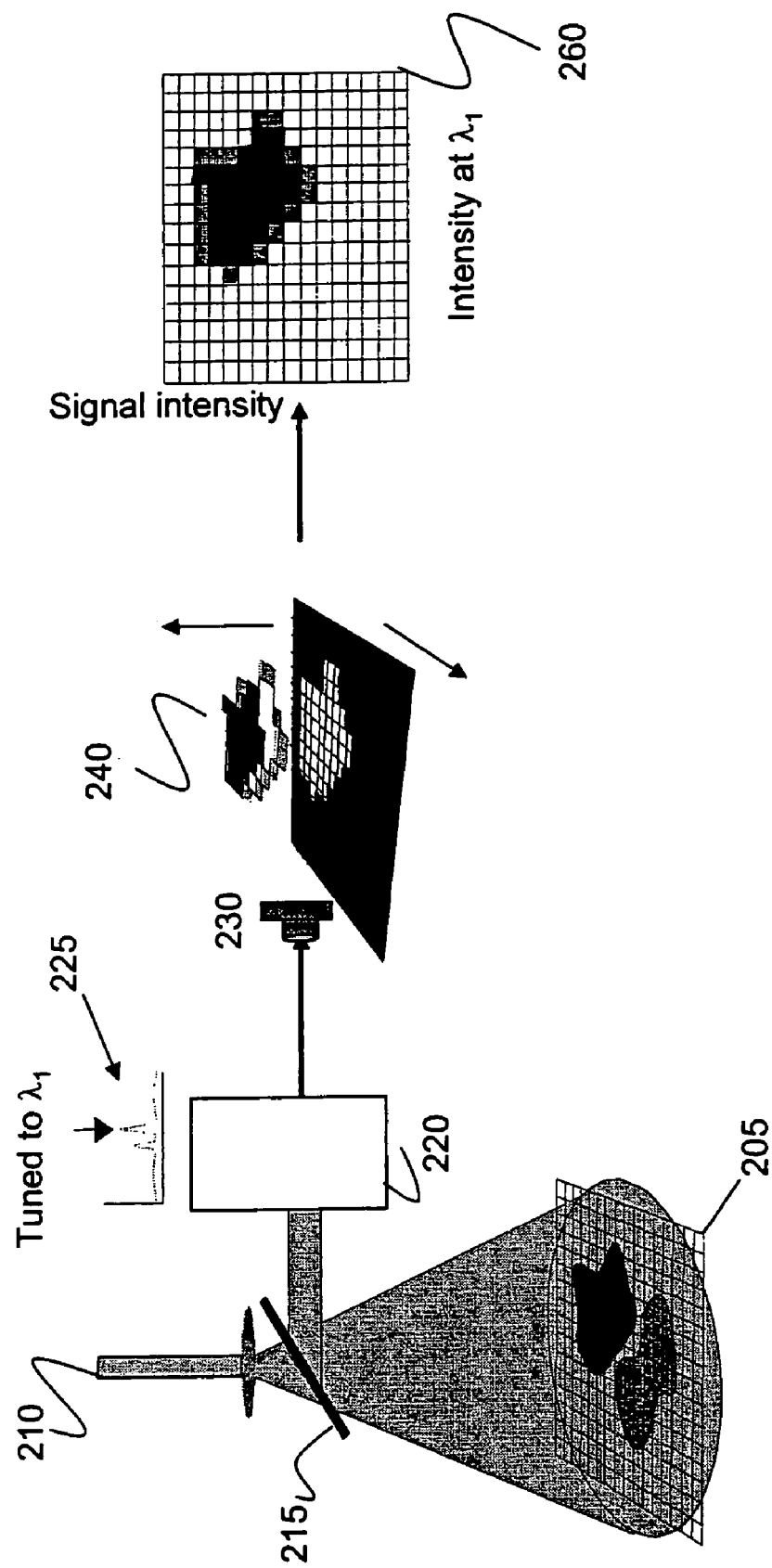
FIG. 2 is a schematic illustration of a conventional widefield scan Raman imaging system.

FIG. 2 is a schematic illustration of a conventional two dimensional Raman imaging system. This system operates somewhat the same as the of FIG. 1, namely illuminating sample 205 using source 210, collecting the reflected image via optics 215, selectively passing a bandpass wavelength via a tunable spectrometer 220 and sampling the image at a photosensitive array 230. However this embodiment collects a two dimensional array of pixel amplitudes during each sampling period.

The spectrometer 220 is effectively an imaging or two dimensional tunable wavelength bandpass filter. By repeatedly sampling and tuning to one wavelength or color and then another, any number of wavelength specific images of the sample can be collected and compared. The spectrometer or tunable filter can be arranged to select one or more specific bandpass wavelengths or to reject specific wavelengths. The passes two pixel dimension spectral image 225 can be collected by a CCD camera 230 to produce several spectral images 240 that can be sampled as pixel data images 260 for each wavelength.

An advantageous tunable wavelength bandpass filter can comprise birefringent crystals and polarizers that are variably spaced and/or rotationally adjusted to select for particular wavelengths and to reject other wavelengths. A liquid crystal tunable filter (LCTF) is an advantageous device for this purpose because its birefringence can be tuned electrically. The liquid crystal filter may be nematic or smectic.

Birefringent materials have different indices of refraction for light energy that is polarized along two orthogonal axes, sometimes known as the fast and slow axes. This has the effect of retarding light polarized along one axis compared to light polarized along the other axis. The extent of retardation depends on factors including the indices of refraction of the material and the thickness of the material along the path through which the light is passed. The difference in the propagation time for light polarized on one axis versus the other axis is a time difference. When considered for different light wavelengths, a given time difference equates to a phase angle difference for any given wavelength, but the phase angle difference is a different angle for two different wavelengths.

Retardation of light polarized on one axis more than light polarized on the other axis can have the effect of changing or re-aligning the polarization state of the light. The extent of re-alignment likewise differs with wavelength. For these reasons, polarization and birefringence are useful considerations for a wavelength bandpass filter.

The polarization state of the light that enters or exits a birefringent crystal may be selectively controlled. If a plane polarizing filter (or "polarizer") is placed to filter randomly polarized light, for example at the input side of the crystal, the passing light can be limited to light energy that is aligned more or less to one or the other of the birefringence axes. If light is aligned to one axis, then rotating the polarizer by 90 degrees aligns the polarizer exclusively to the other birefringence axis. Polarization filters can be used on the input and output sides of a birefringent crystal, to select the nature of the input signal applied to the crystal and to selectively pass only so much of the output as is aligned to the output polarizer.

Assuming that light is initially polarized to a given orientation angle, for example by an input polarizer, then orienting a birefringent crystal at 45 degrees to the orientation angle of the polarizer divides the polarized light into equal vector components, one being aligned to each of the fast and slow axes of the crystal. The retardation of the component on the slow axis relative to the component on the fast axis then changes the polarization state of the light by a rotation angle that depends on wavelength. If an output polarizer is aligned at an appropriate angle for a given wavelength, then that wavelength is transmitted whereas other wavelengths are not.

By manipulation of the alignment of polarizers and birefringent crystals, one can control the allocation of light energy to vector components aligned to the fast axis and the slow axis of the birefringent crystal at each stage. The birefringence of the crystal at each stage retards one of two vector components relative to the other, inducing a phase difference between components on the fast and slow axes of that crystal. The phase retardation between the two components corresponds to a change in the polarization alignment of the light signal, i.e., a change in the angle at which the vector sum of the two components is aligned relative to a reference angle. This change in the polarization state or vector sum angle is specific to wavelength.

There are different ways in which these aspects of light and polarizers and birefringent crystals can be employed as wavelength bandpass filters. In an arrangement including polarizers, a particular wavelength that is passed through a birefringent crystal may be subjected to a polarization change of a specific rotational angle. Other wavelengths are rotated in polarization state by different amounts. By placing a polarizer aligned at that angle on the output of the birefringent crystal stage, only a specific wavelength is passed. Successive stages improve the resolution of the filter.

Figure 3:
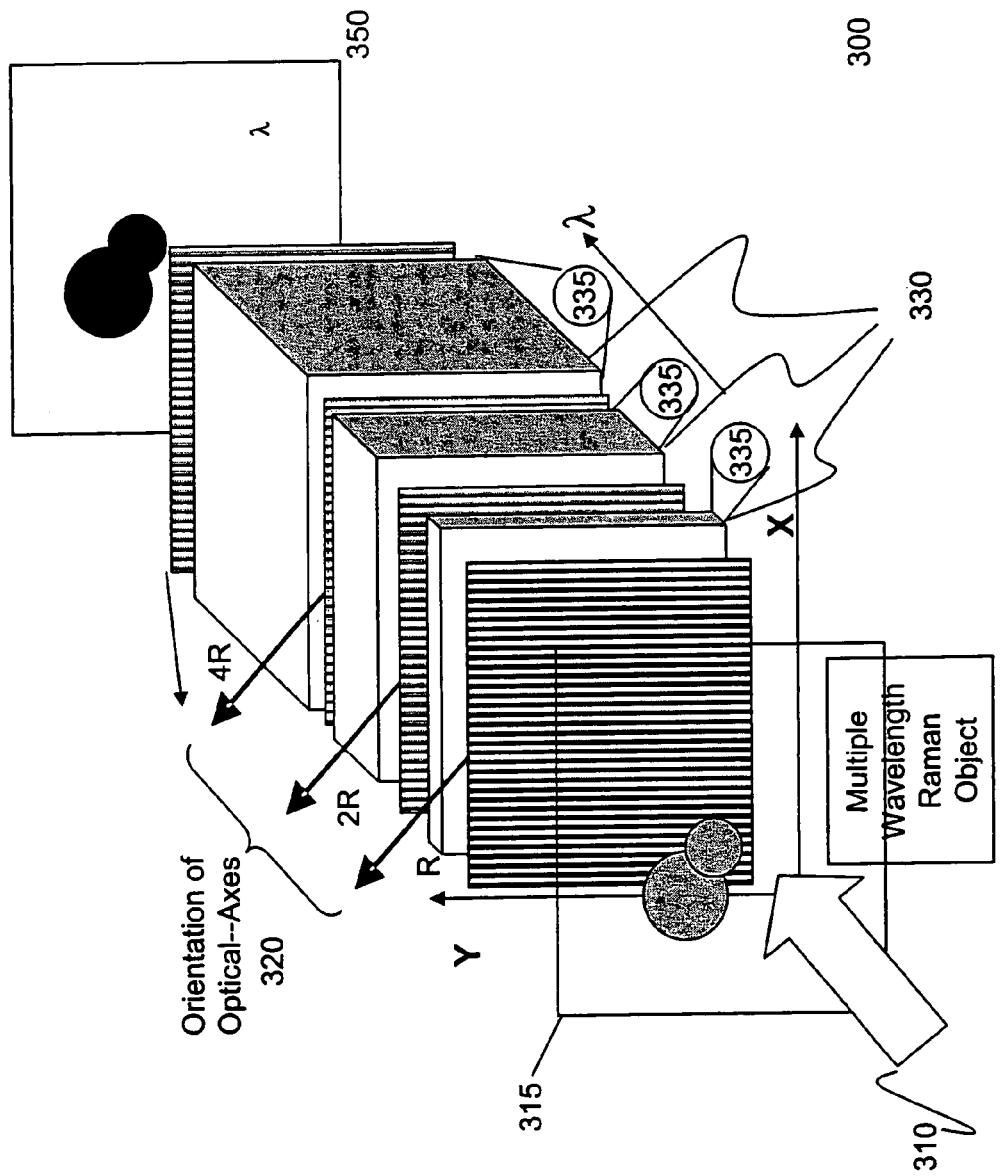
FIG. 3 is a schematic representation of a three-stage conventional Lyot liquid crystal tunable filter.

Some types of wavelength specific filters that can use liquid crystal tunable elements include the Lyot, Solc, Evans and Fabry-Perot wavelength filter configurations, as well as hybrids that employ combinations of the associated elements or additional elements. An LCTF Raman imaging systems using a Lyot filter design for selecting a wavelength spectrum 225 is shown in FIG. 3. The Lyot configuration is an example, and it should be appreciated that the invention is applicable to other LCTF configurations, including but not limited to those mentioned above.

Further, a controller for controlling LCTF detector and shutter as well as a CPU, display unit, key pad and software are conventionally used with the system of FIG. 3. The time for collecting a CCD image and the time for tuning the wavelength bandpass between images both contribute to the time needed to collect a number of wavelength specific images. The image from the detector can be a 2-D image (X,Y) at a given selected wavelength ($\lambda$). The LCTF wide-field is capable of producing a 512×512 pixel image, for example.

As stated, conventional tunable filters can use a Lyot filter. A typical Lyot filter, shown in FIG. 3, includes a set of birefringent crystals between two polarizers placed at 45° to the optical axis of the birefringent material. The bandpass wavelength is a function of the thickness of the crystals, among other factors. Entering light from the polarizer is divided evenly between ordinary and extraordinary polarizations by the 45° alignment. The polarizations propagate with different phase velocities due to the birefringence. This alters the polarization alignment of the light energy as a function of wavelength. For a given thickness of birefringent crystal, only one wavelength (or set of spaced wavelengths) is aligned to pass through an exit polarizer. Thus, the filter produces a comb of frequencies. The bandpass wavelength and separation between the "teeth" of the comb depend on the length of the birefringent crystal. In a liquid crystal, the effective optical length is tunably changeable for the polarization component aligned to the extraordinary axis. In this way the bandpass wavelength can be tuned.

A Lyot filter employs multiple birefringent crystals of different lengths, specifically R, 2R, 4R, etc., with polarizers between each crystal. A Solc filter uses equal crystal thicknesses, input and output polarizers only (no interleaved polarizers) and a relative angular orientation between crystals that divides the relative orientation between the input and output polarizers equally among the crystals.

In FIG. 3, sample 315 which can have a multiple wavelengths Raman image receives emitted photons 310 to form scattered photons. The photons scattered by the sample enter Lyot filter 300 which includes four polarizers 320 and three birefringent optical elements 330 defining successive stages. At each stage, an entry-side polarizer 320 acts as an optical filter to pass light at a polarization orientation that is aligned to the polarizer and to block light at the orthogonal orientation. The subsequent birefringent element 330 is oriented at an angle to the preceding polarizer 320, particularly at 45°. Thus, equal vector components of the light passed through the polarizer are aligned to each of the ordinary and extraordinary axes of the birefringent element 330. Orientation of the optical axes 320 for an exemplary Lyot configuration of wavelength bandpass filter is shown in FIG. 3. Other configurations are also known.

The polarization components aligned to the ordinary and extraordinary axes of the birefringent elements 330 propagate with different phase velocities due to the birefringence of elements 330. Also, the birefringent elements 330 at each stage are of a different thickness. By retarding orthogonal components of the light signal, the polarization orientation of the light is realigned to an angle the depends on the wavelength of the light. At the next polarizer encountered, light only at one set of wavelengths is aligned to pass through the next polarizer, which functions as the output polarizer or selector for the preceding stage and as the input polarizer for the next stage. the thickness of the respective birefringent elements 320 and the alignments of the birefringent elements are chosen so that each stage further discriminates for light at the same bandpass wavelength.

The bandpass wavelength is tunable by applying control voltages 335 to the birefringent elements 330, which preferably comprise liquid crystals. The effect of changing the birefringence of the liquid crystals is to shorten or lengthen the effective optical path encountered by the component of the light aligned to the extraordinary axis while leaving the effective length unchanged for the ordinary axis. This is much the same as controllably adjusting the effective thickness of the birefringent elements 330. Each birefringent liquid crystal element 330 of the Lyot filter is coupled to a voltage source 335 for tuning the bandpass of the birefringent elements 330. In a Lyot configuration, the thicknesses are integer multiples (R, 2R, 4R, etc.) and can be controlled in a coordinated manner, for example being coupled to the same control voltage source 335, so as to keep the effective thicknesses equal to the required multiple. In other similar configurations the thicknesses can be otherwise related (for example as in a Solc configuration wherein the thicknesses are equal) and controlled so as to maintain the required relationship, such as to be coupled in parallel to the same driving voltage source.

It is conventional in multispectral imaging to collect individual images in which the entire image is collected at one wavelength bandpass, for comparison with other images at different wavelength band passes. According to one embodiment of the present invention, a novel tunable filter is arranged to tune to different wavelengths across the X-Y image field. The filter may have one or more stages with at least one stage having a wedge-shaped liquid crystal cell or other shape in a tunable configuration having a bandpass wavelength that is not uniform across the surface of the filter, examples being shown in FIGS. 4B, 4C, 6, 7, etc. In these configurations, a wedge shaped or similarly structured birefringent element has a thickness that differs across its operative area. The wedge shaped birefringent element can be tunable and optionally is associated with a uniform (non-tunable retarder). Optionally, a non-tunable wedge shaped birefringent retarder can be combined with a tunable birefringent element of uniform thickness. By combinations of controllable-birefringence and fixed-birefringence elements in uniform an varying thickness along the optical path, different positions in the field are tuned to different bandpass wavelengths.

Figure 4A:
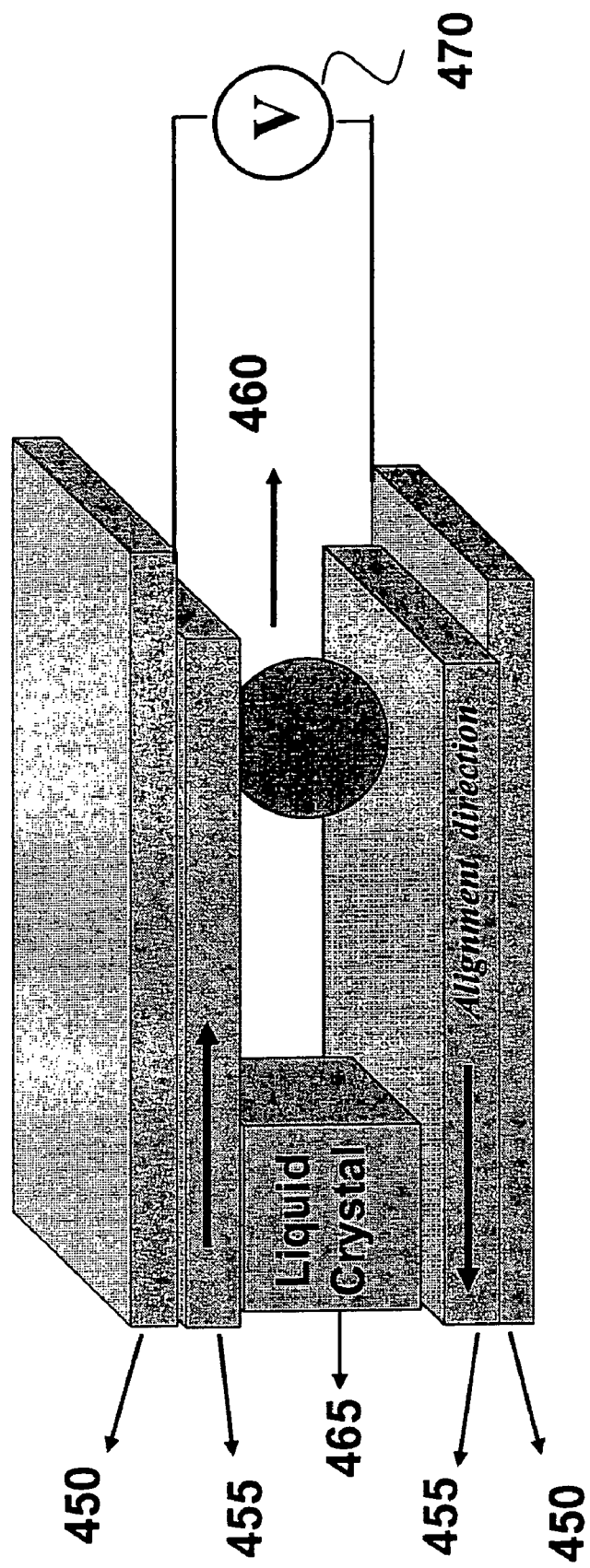
FIG. 4A schematically illustrates a uniform liquid crystal cell of an electronically controlled birefringence cell.

FIG. 4A schematically shows the elements of a liquid crystal cell of a uniform thickness and electronically controllable birefringence. The uniform thickness liquid crystal shown in FIG. 4A can form a subunit or cell of a liquid crystal filter having plural elements that are stacked along an optical path or arranged adjacent to one another in a pixilized configuration. Each subunit has an associated transparent plate 450, for example of fused silica or glass. On the side of plate 450 that faces liquid crystal cell 465, glass plate 450 has a conductive coating (not shown) such as indium tin oxide (ITO), which is nearly transparent but conducts sufficiently to apply an electric field to liquid crystal material 465 in the element. The conductive surfaces are coupled to leads that provide a driving voltage for each subunit by operation of the LCTF controller 470. Between the ITO transparent electrode and the liquid crystal 465, the plate 455 is further coated with an alignment layer. The alignment layer is physically treated, typically by rubbing or buffing, to induce a direction at which the molecules of the liquid crystal material tend to align. This alignment direction determines the director orientation of the liquid crystal and is used to orient the liquid crystal element 465 relative to the polarized light being transmitted.

Spacer 460 is provided to maintain the thickness of the zone between the alignment layers 455, occupied by the liquid crystal material 465. The spacer 460 is shown as a sphere but could be a different shape such as a cylinder or the like. The spacer can be a polymer or silica glass of the type produced in large numbers with relatively uniform size. Spacers 460 can be admixed into the liquid crystal material to provide a minimum thickness to which the liquid crystal 465 can be compressed. The spacer materials may be around the periphery of the liquid crystal material in the element (inside the glue edge) or distributed through the liquid crystal material. The spacers can be used to keep the cell gap uniform (although it optionally can be intentionally made slightly slanted to avoid interference fringes arising from coherent laser light). The ratio of volumes of the spacer material to the liquid crystal material is low enough to minimize the effect on light propagating through the liquid crystal material. When the liquid crystal material is contained between the alignment layers, the molecules in the liquid crystal layer near plate 450 line up parallel to plate 450 and to the direction of alignment of alignment layer 455. The liquid crystal cell can be configured as an electrically controlled birefringence (ECB). The liquid crystal may also be a nematic or smectic liquid crystal.

Figure 4B:
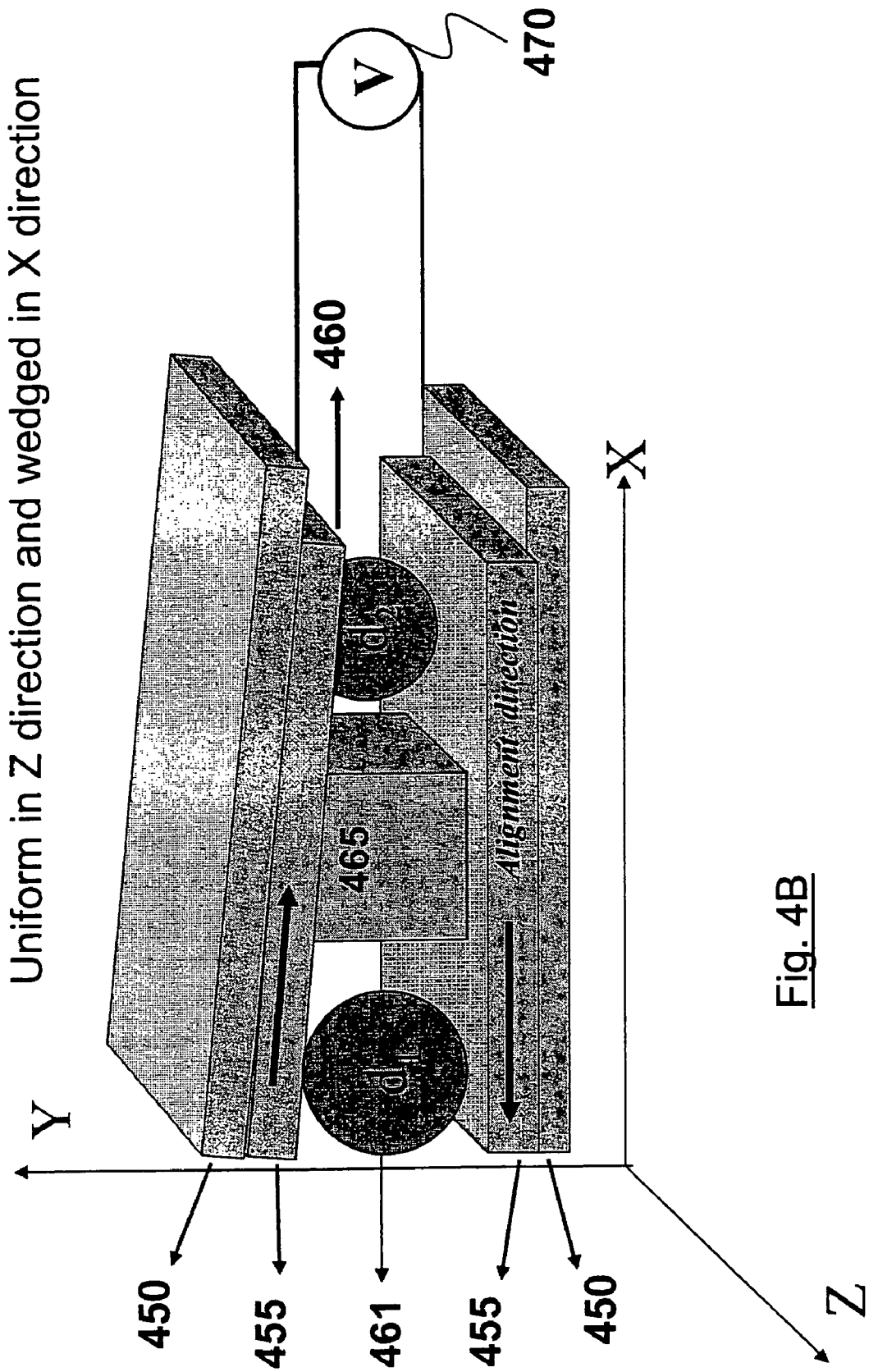
FIG. 4B schematically illustrates a wedged liquid crystal cell of an electronically controlled birefringence cell.

In contrast to the uniform liquid crystal cell of FIG. 4A, FIG. 4B schematically illustrates a wedged-shaped liquid crystal cell of an electronically controlled birefringence cell. In the embodiment of FIG. 4B, spacers 460 and 461 are of different sizes, such that the plates 450 are not parallel and the overall cell has a wedge-shape. That is, spacers supporting the plates on opposite sides of the liquid crystal element are or different thicknesses, and as a result, the retarder in FIG. 4B defines a wedge with thickness that varies with respect to the point at which light passes through the retarder element. Light passing through the retarder element will encounter a different thickness at a point closer to one spacer or the other, and across the distance between the spacers will encounter a thickness that varies linearly (because the plates in this case are flat). Thus, retardation is a function of the relative diameters of the spacers ($d_1$, $d_2$) as well as the effective refractive index ($n_{eff}$) of the cell.

Figure 4C:
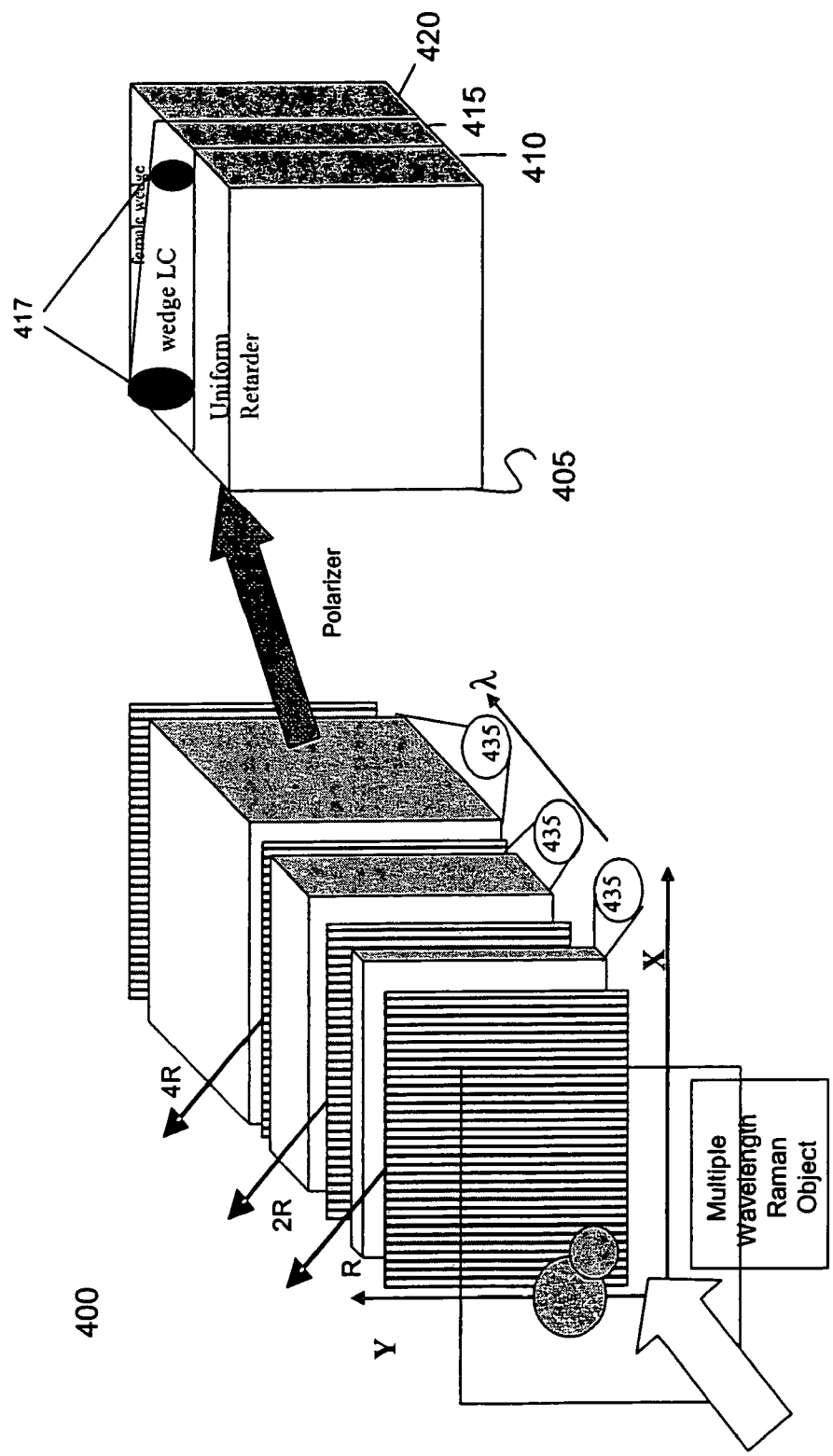
FIG. 4C is a schematic illustration of an optical device and an optical stage according to one embodiment of the disclosure.

FIG. 4C is a schematic illustration of an optical device and an optical stage according to one embodiment of the disclosure. In the embodiment of FIG. 4C, optical device 400 is shown has having three optical stages. At least one of the stages 405 is arranged to provide for different effective retarder thickness across the X-Y operative area in which light can pass through the stage. The stage 405 shown has a uniform retarder 410 coupled to wedged liquid crystal 415. The wedged liquid crystal 415 receives complementary female wedge 420 to form a geometric cube. The wedged liquid crystal is shown to have two spacers 417. Conventional liquid crystal material can be used for this application. Voltage source 435 can be coupled to the liquid crystal segment of stage 400 to fine-tune the birefringence of stage 405. Uniform retarder 410 can be made of quartz, lithium niobate ($LiNbO_3$) or a polymeric material having the desired birefringent optical characteristics. Female wedge 420 can be a homogeneous optical transparent glass or a polymeric material having similar optical properties.

The placement of the female wedge is optional. Although in the exemplary embodiment of FIG. 4C, only one stage of the filter 400 is shown as having a wedge-shaped liquid crystal segment, it should be noted that the disclosure is not limited thereto and more than one stage can be configured according to the principles of the disclosure. Moreover, the principles of the disclosure are not limited to having a three-stage filter and may include more (or less) stages than shown in FIG. 4C. Indeed, the principles illustrated in the exemplary embodiment of FIG. 4C can be used with pixelized and/or columnized LCTF. The number of liquid crystal cells can be a function of the application. For example, for a Lyot filter, each stage may generally contain one liquid crystal cell while for an Evans-type filter each stage may contain multiple liquid crystal cells.

In one embodiment, the disclosure relates to a multistage filter where each stage includes a wedge-shaped liquid crystal cell and, optionally, a complementary optical transparent wedge-shaped glass. Moreover, the liquid crystal cell can be coupled to a voltage source to enable further fine-tuning of the cell. The filter can be tuned by using the voltage source and a controller.

Figure 5:
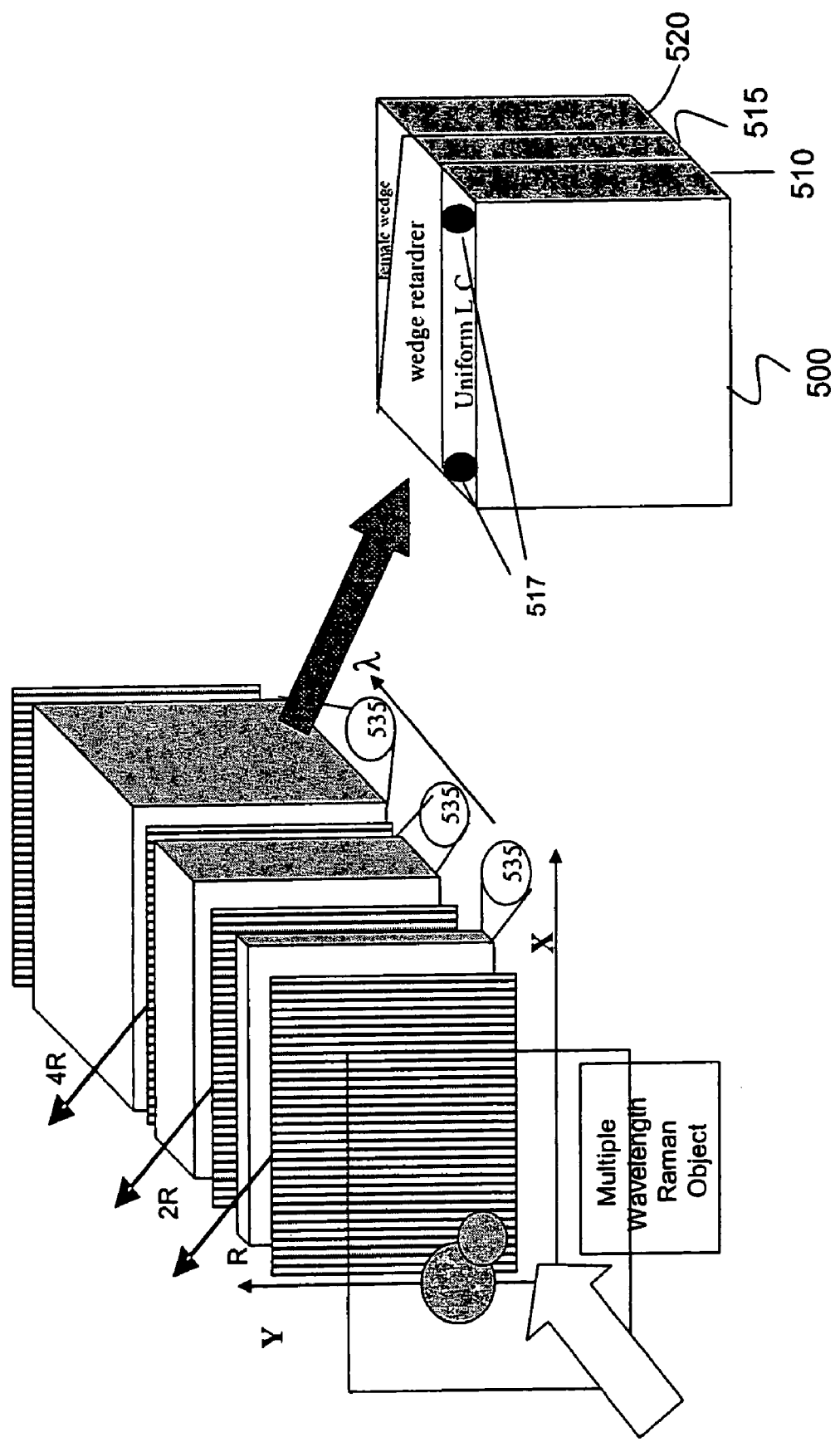
FIG. 5 is a schematic illustration of an optical stage according to another embodiment of the disclosure.
Figure 6:
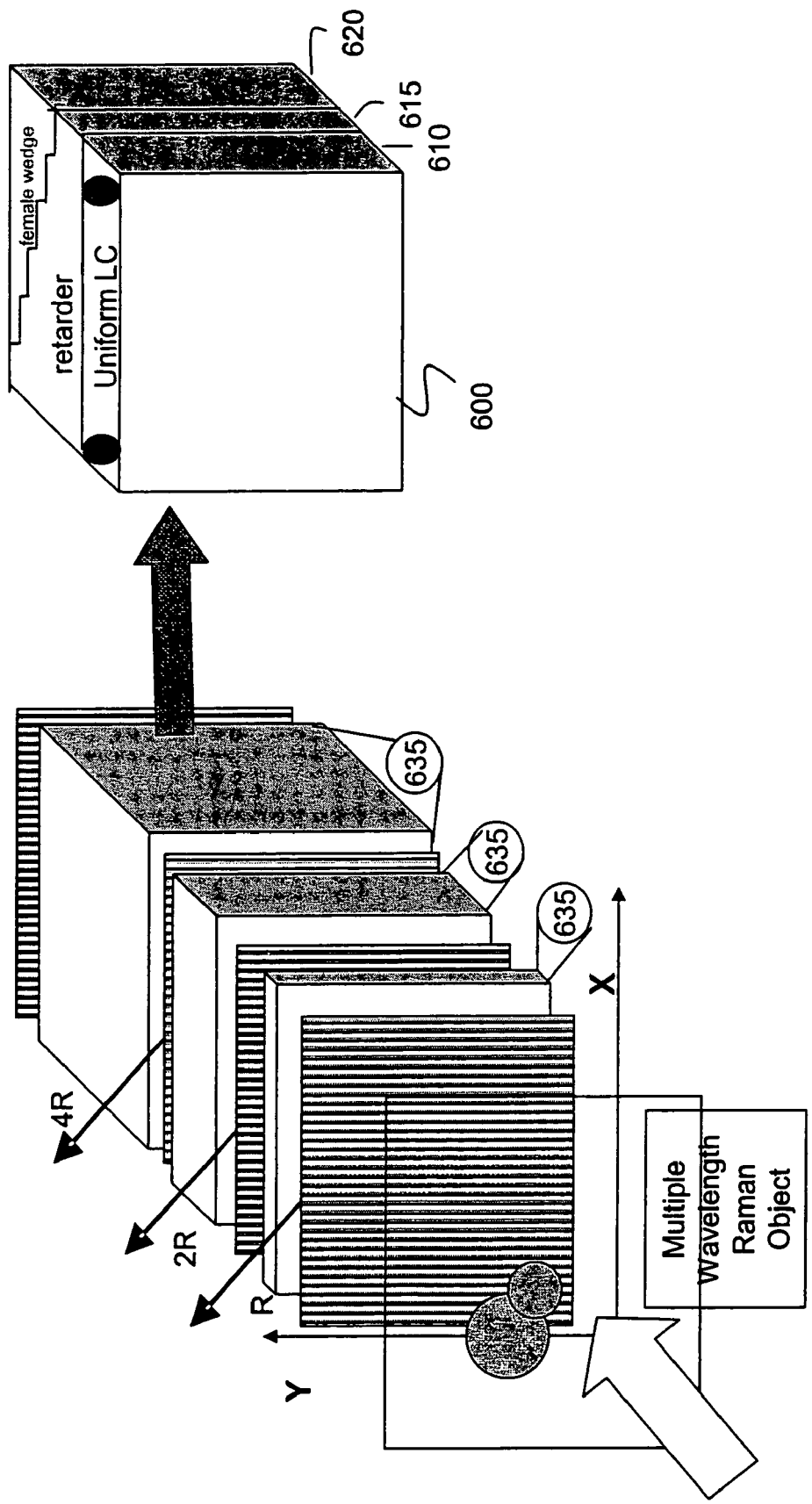
FIG. 6 schematically illustrates a stepped LCTF device for un-patterned Raman imaging or other chemical imaging applications according to another embodiment of the disclosure.

In the embodiments with wedge-shaped elements as shown in FIGS. 4 and 5 and with stepped thickness elements as in FIG. 6, across an X-Y image field, there is a difference in thickness of the operative retardation element(s) along the light propagation axis Z, for different points in the X-Y field. The difference in thickness can occur in the controllable birefringent liquid crystal element. The difference in thickness alternatively or additionally can occur in a retarder of fixed birefringence, used with another element that is controllable for tuning. In each of these situations, light traversing the element along a line parallel to the Z axis at a given point in the X-Y image field, is subjected to a different phase delay, due to the difference in thickness Z, from the phase delays of other points in the X-Y image field. As a wavelength bandpass filter, a result of the wedge-shaped element is that the center wavelength that is passed by the filter differs at different points across in the X-Y field.

In the embodiments of FIGS. 4-6, the wedge shape has a thickness that is either linearly or stepwise varied from a minimum thickness at one extreme of one of the X or Y axis to a maximum thickness at the other extreme. The minimum thickness can taper to some non-zero minimum thickness or can taper to a sharp edge. It is also possible that the thickness can vary in both X and Y, for example with the minimum and maximum thickness occurring at opposite corners rather than adjacent corners. That structure would be equivalent to rotating the wedge element by 45° from the orientation shown. Other variations in thickness are potentially applicable to vary the wavelength passband at different points in a field, such as conical shapes, pyramids, truncated cones or pyramids, etc.

The thickness variation of wedge shape according to this aspect should be distinguished from the technique of slanting a birefringent element used with a monochromatic (laser) light source as a means to prevent fringing of a monochromatic image due to interference effects. According to the present invention, and unlike the anti-fringing technique, a thickness variation is introduced into the tunable or fixed birefringence elements so as to cause the device to tune to different wavelengths at different X-Y locations on an image field at the same time. This is accomplished in the exemplary embodiments with continuously wedge shaped tunable or fixed retarders (the wedge shape potentially resulting in a slanted surface or interface), or a step-wise wedge shape (e.g., FIG. 6).

FIG. 5 is a schematic illustration of an optical stage according to another embodiment of the disclosure. According to the exemplary embodiment of FIG. 5, optical stage 500 comprises uniform liquid crystal 510 coupled to wedge retarder 515 and female wedge 520. Spacers 517 are shown along an axis of the liquid crystal 510 device to maintain a uniform thickness. As with the exemplary embodiment of FIG. 4, female wedge 520 is complementary to wedge-shaped retarder 510 and may be used optionally. In addition, a voltage source 535 is provided to supply a programmed voltage to the uniform liquid crystal segment 510.

In another embodiment, the disclosure relates to a tunable filter comprising several uniform stages. Each uniform stage may include a fixed wedge-shaped retarder, and optionally, a homogeneous optical transparent wedged glass. The wedge-shaped glass can be configured to complement the wedge-shaped retarder so that when combined, the two form a three dimensional rectangle. Each stage may further include a first polarizer affecting photons coming into the retarder and a second polarizer affecting the photons leaving the optional transparent glass. The tunable filter may include a stack of N stages. In another embodiment, a stage according to the principles disclosed herein may be used as a part of a stack configured as a Lyot filter, a Solc filter, an Evan filter or a hybrid filter. As is known to one of skill in the art, a hybrid filter may contain many stages (at least two stages). Some of the stages in a hybrid filter may include Lyot filter, Solc filter, Evans filter or Fabry-Perot interferometer.

FIG. 6 schematically illustrates a stepped LCTF device for un-patterned Raman imaging or other chemical imaging applications according to another embodiment of the disclosure. In the exemplary embodiment of FIG. 6, stage 600 includes uniform liquid crystal 610 optically communicating with retarder 615 having a stepped profile (herein "stepped retarder"). The stepped retarder 615 receives a complementary female wedge 620. As with the exemplary embodiments of FIGS. 4 and 5, stage 600 may be coupled to voltage source 635 for better optical modulation. The embodiment of FIG. 6 can be modified to include a symmetric uniform retarder, a stepped liquid crystal and a complementary female wedge. As before, the female wedge can be a homogeneous optical transparent glass or a composite having similar optical properties.

In one embodiment, a tunable filter can be configured to include N stages. Each stage can have a male stepped-retarder and a complementary female homogeneous transparent glass. A polarizer can cover each face of the three dimensional rectangle formed by combining the retarder and the complementary glass. A plurality of stages can be assembled in an order of increasing thickness to form a tunable filter. In this embodiment, the filter resolution is determined by the number of stairs as well as the number of stages in the filter.

Figure 7:
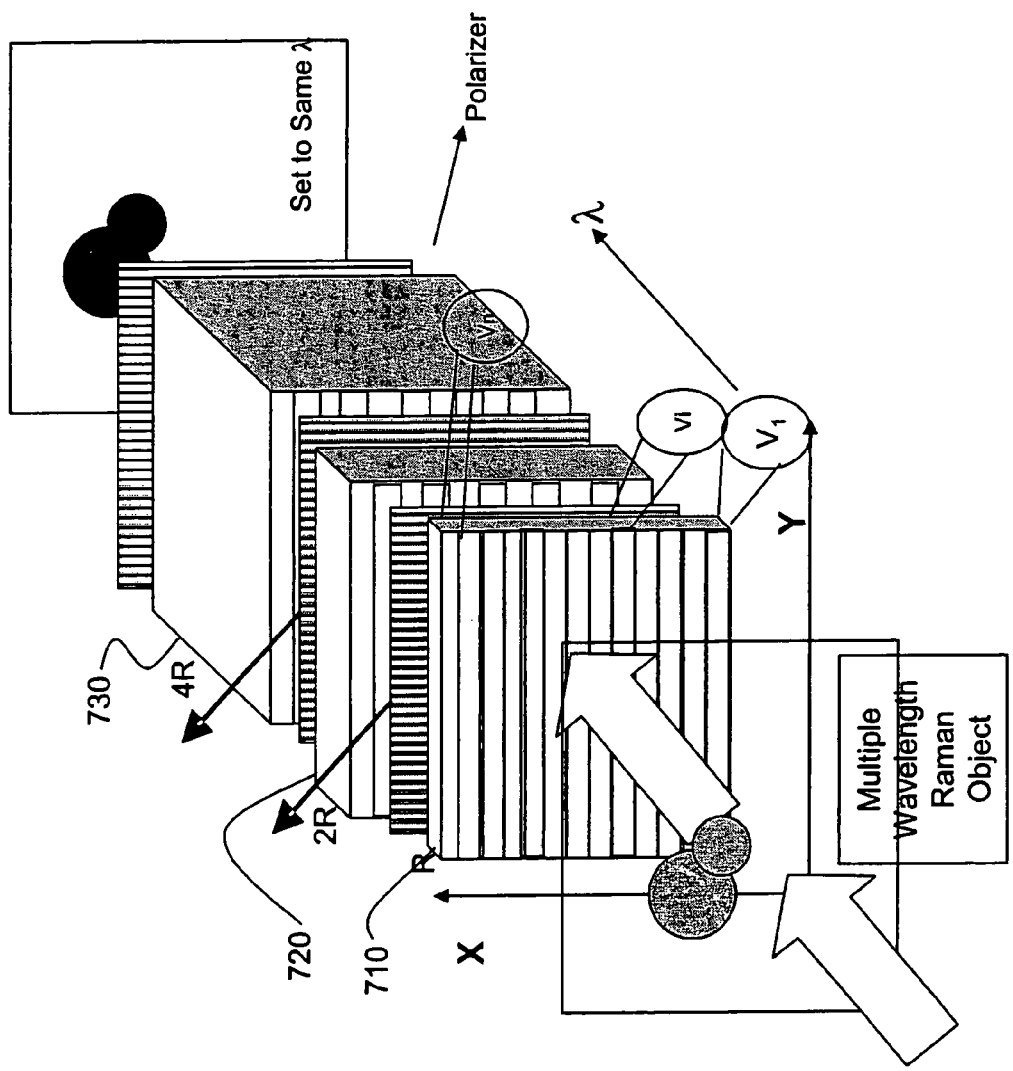
FIG. 7 is a schematic illustration of a columnized LCTF device for Raman imaging or other chemical imaging applications according to another embodiment of the disclosure.

FIG. 7 is a schematic illustration of a LCTF device for Raman imaging or other chemical imaging applications in which the thickness variations occur in striated bands that extend across the X-Y field of the filter element, horizontal band or striations being shown. FIG. 7 shows a three-stage Lyot-type filter according to one embodiment of the invention and is similar to the previous embodiments in that each stage may include a liquid crystal cell and an optional retarder element such as a birefringent crystal. Each stage is shown to be interposed between two polarizers (at entry and exit points of the stage). The birefringent crystal and liquid crystal have optical axes aligned at 45° to the orientation of an input polarizer (the initial polarizer not shown in FIG. 7). The conductive layer (normally indium tin oxide) can be provided on at least one glass substrate of the liquid crystal cell patterned in rows (or columns) of a given width. Moreover, each row or column can be coupled to the same or a different control voltage by means of individual control voltage sources $V_1$ to $V_n$. In one embodiment, the columns (or rows) of each stage are aligned with similarly situated columns (or rows) of other stages. Referring to FIG. 7, stage 710 is receiving voltage sources $V_1, V_i \ldots V_n$. The filter can be used as a conventional tunable filter by setting the voltages to each column equal in the same stage, and the filter can be arranged to tune each column or row to a different voltage for providing a different wavelength bandpass. The successive stages 710, 720, 730 are operated in coordination to pass the same wavelength through each aligned column (or row) in the stacked stages.

Figure 8:
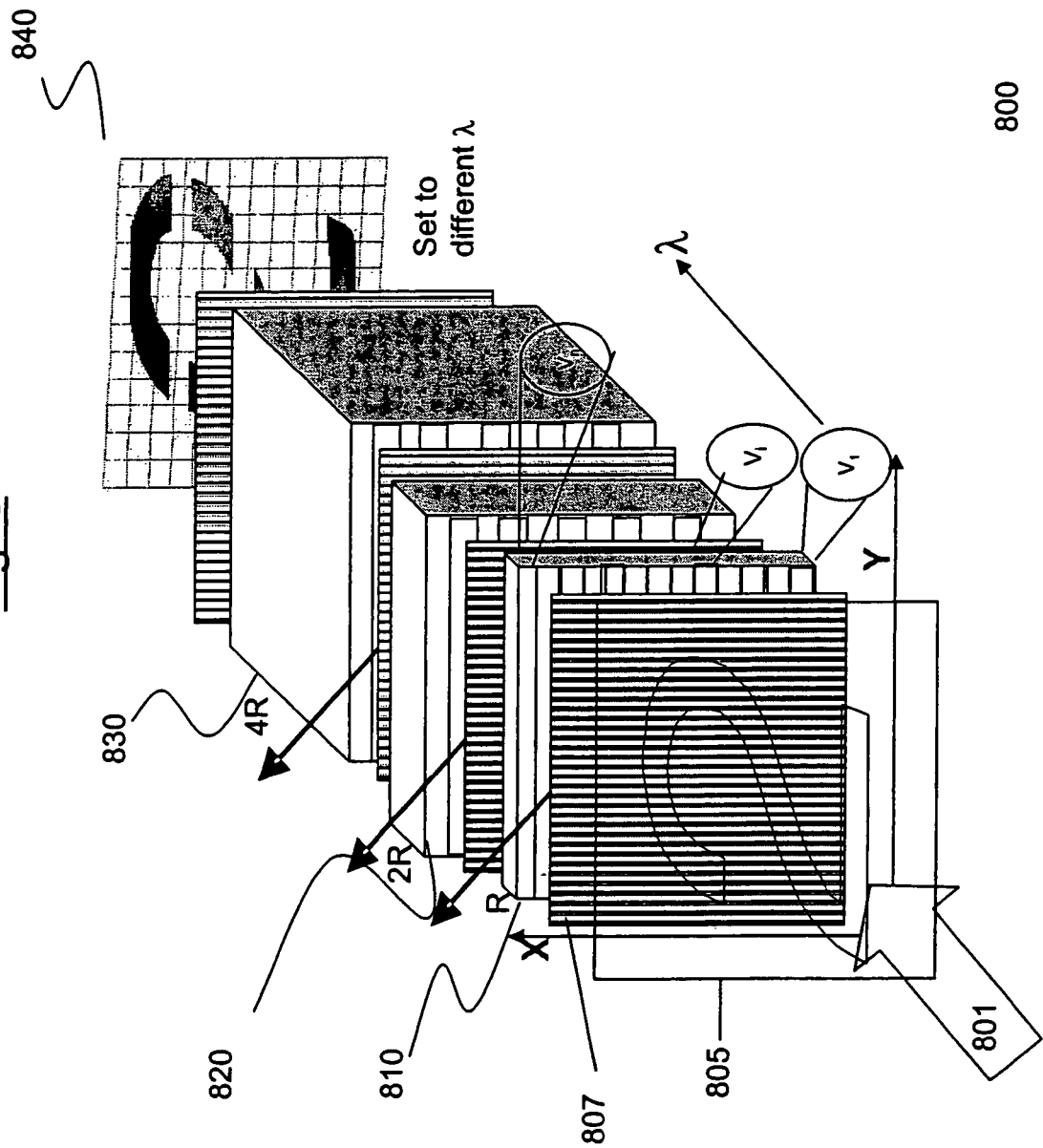
FIG. 8 is a schematic illustration of a columnized LCTF device for Raman or other chemical imaging applications according to one embodiment of the disclosure.

By applying different voltages across various columns (or rows) of the liquid crystal cell of stage 710 and related columns (or rows) in the following stages 720, 730 such that a substantially independently tunable filter configuration is formed through the columns (e.g., the Lyot configuration with thicknesses R, 2R, 4R), a different bandpass ($\lambda_1$-$\lambda_n$) can be defined at different columns (which is shown in FIG. 8. and is further discussed below.) This translates the imaging LCTF into a dispersive spectrometer. Although the first stage 710 is shown as coupled to voltage sources $V_1$ to $V_n$, the principles of the disclosure are not limited thereto and stage 710 can be devised to receive only one voltage source. Moreover, the voltage sources can be applied along the various columns of the liquid crystal segment of stage 710. Applying a voltage source is not limited to only one stage of the filter and can be devised such that each of the various stages are driven by a voltage source. The various columns (or rows) can also be binned together so that part of the image received from CCD is at, for example, wavelength 1 while another part of the image received from CCD is at wavelength 2. Stage 710 can also include a uniform retarder, a stepped or a wedge retarder and a complimentary wedge as described above. A black matrix mask can be placed on the exit polarizer of the last stage to prevent light leakage at inter-pixel regions or inter-column regions, when the filter is not tunable.

FIG. 8 is a schematic illustration of a columnized LCTF device for Raman or other chemical imaging applications. Referring to FIG. 8, first stage 810 is coupled to several voltage sources $V_1$-$V_n$. Each of voltage sources $V_1$-$V_n$ may operate independently of the others to supply power to electro-optically tuned liquid crystal cell of stage 810. This results in a dynamic LCTF with high spatial resolution and a filter that can be operated to distinguish by image or by wavelength. By providing different voltages across the column (or rows) of the liquid crystal segment as well as the related columns (or rows) in the subsequent stages, the tunable filter can be reconfigured along the X axis to provide a 1-D spectrum (Y, λ) at certain location X as a function of the activation state of the LCTF. The liquid crystal used in the columnized system of FIG. 8 can be either nematic or smectic. Although the embodiment of FIG. 8 depicts only one of the three stages as receiving separate voltages, the disclosure is not limited thereto and stages 820 and 830 may also be configured for columnized tuning.

The filter of FIG. 8 can be coupled to a photon emission source, a photon detection source, an optical lens and a processor to form a system for obtaining a spatially accurate wavelength-resolved image of a sample having a first and a second dimension. The photon detector may include a charge-coupled device, a complementary metal oxide semiconductor, a charge injection device, an intensified charge injection device, an electron multiplying charge-coupled device, a silicon photo diode, a silicon avalanche diode and a focal plane array. The photon emission source may be laser, a light emitting device or a fluorescence device.

Figure 9:
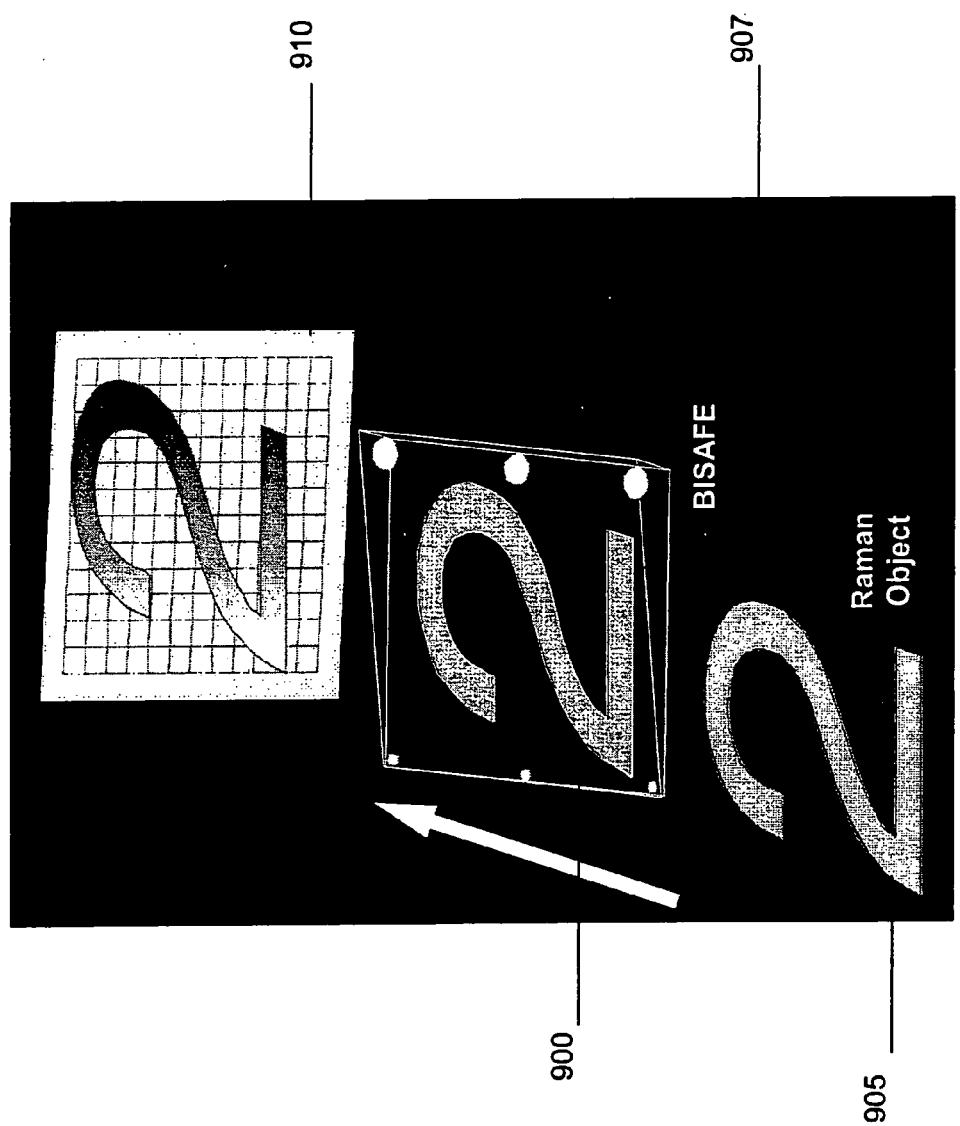
FIG. 9 is a schematic illustration of an un-patterned Raman imaging or other chemical imaging applications system according to another embodiment of the disclosure.

FIG. 9 is a schematic illustration of an un-patterned Raman imaging or other chemical imaging applications system according to another embodiment of the disclosure. Referring to FIG. 9, optical filter 900 receives scattered photons from object (optionally a Raman Object) 905 and produces spectrum 910. The wedged-shaped liquid crystal filter 900 may be coupled to a voltage source 907. Applying voltage 907 to filter 900 changes crystal retardation at positions along filter 900. By applying a voltage to filter 900 at various positions along the lateral length of the filter, filter 900 can produce variable retardation. In an optional embodiment, each of rows 1 through N can receive a different voltage.

In FIG. 9, the wedge design can create a series of bandpass zones. Each bandpass zone may allow a different wavelength ($\lambda_1$-$\lambda_n$) through at different locations of filter 900 in FIG. 9. Similar to the exemplary embodiments of FIGS. 4 and 5, the bandpass zones may be disposed in horizontally in the X direction. The different bandpass zones allow filter 900 to operate as a dispersive spectrometer. The resolution of the filter can be a function of the CCD camera's pixel size and the wedge angle of the filter for each stage (if a multi-stage filter is utilized). The additional liquid crystal cell in each stage can add the feature of tunability to the filter so that each bandpass zone of the filter can be tuned independent of the other zones. As compared with the embodiments of FIGS. 4C and 5, where voltage is applied to the entire liquid crystal cell such that retardation of each stage satisfies a Lyot filter configuration (i.e., R, 2r, 4R, etc.), the embodiment of FIG. 9 can be configured to generate a series of bandpass zones ($\lambda_1$-$\lambda_n$) at different positions of the filter along the X direction (for example at locations $X_1$-$X_n$ not shown). The retardation of the liquid crystal cell may be changed by changing the applied voltage thereby allowing the liquid crystal cell to act as a variable retarder. Therefore, at each position $X_i$ (not shown) the bandpass wavelength can be changed by changing the voltage to the liquid crystal cell. The final two-dimensional image 910 at a particular wavelength $\lambda_i$ may be constructed by a computer by combining, for example, the bandpass zones that are passing the same wavelength $\lambda_i$.

Figure 10:
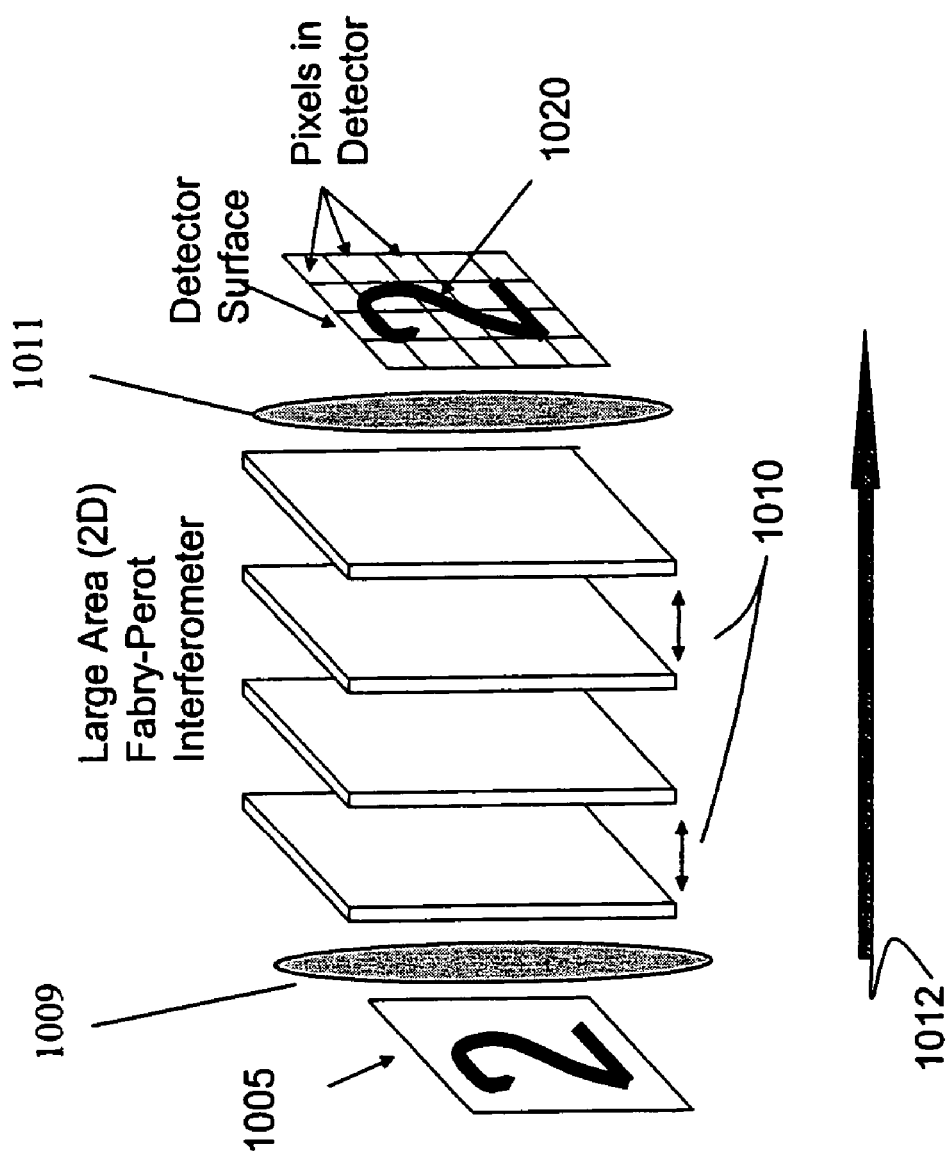
FIG. 10 is a schematic illustration of imaging system using tunable Fabry-Perot.

FIG. 10 is a schematic illustration of a compact imaging filter for the handheld system using a tunable Fabry-Perot micro opto-electromechanical system. The sample 1005 shown here as the numeral 2 is an opaque surface which is irradiated by light and either reflectively scatters incident light or absorbs light energy and re-emits the energy at characteristic wavelengths, in all directions. The rays emanating from an arbitrary point (x,y) on sample 1005. An optical system generally represented in the drawing by lens 1009 directs rays from the point (x,y) in a direction 1012 through one or more compact 2-D Raman imaging filter elements 1010, two being shown in the example. A receiving optical system generally represented in the drawing by lens 1011 is used to obtain a spatially accurate wavelength resolved image of the sample, on the surface of a detector 1020.

In FIG. 10, the imaging filter comprises a series of filter elements having paired thin partially transparent parallel Si plates separated by air so as to cause the pair(s) each to define an optical cavity. The plates can be fabricated by micro-machining and are movable by a micro-electromechanical positioners (not shown) to adjust the cavity thickness between the plates and thereby to tune the resonant wavelength of the cavity. Preferably, two or more pairs of substantially reflective (but less than 100% reflective) plates 1010 form the cavities of one or more Fabry-Perot interferometers. The plural cavities are set to the same cavity spacing. Rays oriented normal to the plates at the resonant wavelength are passed and other wavelengths are reflected backwards along the optical path.

Optical plates 1010 can be fabricated from a planar Si wafer and the wafer can be configured to form a supporting frame by micro-machining steps, for example using chemical or ion beam etching. By additional processing steps known to those skilled in the art, connecting members are formed between the supporting frame and the thin substantially reflective Si plate (e.g., along the sides and corners of each Si filter element) so as to provide electronically controllable positioning actuators for setting the cavity thickness(es). These actuators (not shown) move one or both optical plates 1010 in pairs defining the Fabry-Perot interferometers. The plates 1010 can be moved uniformly in and out of the plane of the respective supporting frame (i.e., in a direction parallel to the optical axis and normal to the parallel planes of the optical plates), for setting the cavity thicknesses as indicated by the arrows.

In one embodiment, the actuator can be activated by a voltage source. The actuator can be switchable between discrete tuning positions (cavity thicknesses) or capable of adjustment to a desired point in a range of actuator displacement positions, depending on the desired outcome. This set of planar structures containing the Si filter elements and onboard actuators are stacked along the optical axis to form a Fabry-Perot imaging filter. In this stack each thin parallel Si plate is parallel to and aligned with all the other plates so as to all point in a direction parallel to a central optical axis.

The final number of plates can define Fabry-Perot etalons between pairs, or can be odd if the plates of successive pairs are also used as a resonant cavity and thus define another pair. In that event, the spacing of the plates and the spacing between such successive pairs must each be controlled to employ the same resonant spacing. Different combinations of MEMS actuator displacements between pairs of filter elements together with combinations of different stacking distances between sets of plates (such as to form stages) will allow the transmission of a narrow passband of light at a selected wavelength in a range of wavelengths to which the device is controllably tunable.

The filter wavelength $\lambda$ is selected by changing the cavity or distance between each of the Fabry-Perot filter elements in a predetermined manner. The actuator displacements, the spacing between plates and number of plates determines the range of the wavelengths over which transmission is achieved upon actuator changes (i.e., tuning), as well as the wavelength window over which the light at wavelength $\lambda$ is transmitted (i.e., the bandpass.) Bandpasses for such a device can be as narrow as 0.25 nm (high resolution) or up to 10 nm (lower resolution). The ranges of wavelength over which the device operates (i.e., filter different wavelengths of light) can be, for example, between 400 nm and 1800 nm. The design tradeoffs that achieve such performance are selected to optimize the number of elements (cost and simplicity) and the overall transmission function (optical efficiency) for any particular measurement requirement such as Raman, Fluorescence, VIS or NIR chemical imaging.

For Raman, Fluorescence, Visible or NIR operation a particular arrangement of stacks of the plates can be used for which a predetermined set of actuator voltages are known that provide the required wavelength filtering characteristic. For the particular mode of operation the required set of voltages are then called by the computer and applied to the actuators for each wavelength to be imaged. Scanning a set of actuators and acquiring the data over the full image 1020 creates the wavelength resolved spatially accurate image.

Preferably, a 2-D image (X, Y) image of the sample is produced on the detector 1020. The tunable optical cavities produce the image at one wavelength at a time and are controllable for tuning to two or more wavelengths and optionally to selected wavelengths in a range. The tuning speed can be less than 1 sec for changing between cavity spacings and thus selecting for an image at a new wavelength.

The optical systems 1009 and 1011 before and after the Fabry-Perot plates can be used to allow the light scattered or emitted from the sample 1005 to accurately and faithfully reproduce each (x, y) location of the sample 1005 onto the detector plate 1020 at (x', y'). The specific detector pixels form an image or spatially accurate representation corresponding to positions of points in the image of the sample. Optical configurations are possible where transmitted light is discriminated without using optical systems 1009 and 1011 that contain lenses. For example, a stacked Fabry-Perot array wherein each etalon discriminates for wavelength due to the thickness of the cavity in a normal direction has the characteristic of selectively passing only normally oriented rays, thereby effectively collimating the light from the image and providing a spatially resolved image as applied to the detector.

The embodiment of FIG. 10 enables an ultra-compact high resolution Raman or fluorescence imaging device which can be selectively fine-tuned to enable acquisition of a Raman or fluorescence spectrum corresponding to each spatial element of the sample. Individually addressable Fabry-Perot filter elements 1010 can enable acquisition of a Raman or luminescence spectrum corresponding to the spatial elements of sample 1005. When detector 1020 is a CMOS detector, each individual pixel can be sensed independently by tuning the wavelength applied to specific pixel elements which is not possible in typical CCD detector device. Use of such a Fabry-Perot imaging filter is novel in that prior MOEMS based Fabry-Perot Filters have not been capable of performing imaging—only wavelength selection of an optical source. An additional advantage in this invention is that the CMOS detector in this preferred embodiment can be pixel selected so as to apply attention only on the important pixels in the sample—thereby speeding and simplifying collection of the most important data from specific regions of the sample.

The Fabry-Perot filter element not only transmits but in an alternate embodiment can reflect the light to an individual pixel of a CMOS sensor to form a single wavelength Raman or luminescence imaging object 1020 of spatially accurate spectrally resolved pixels of the sample. That is, in an alternative embodiment one or more Fabry-Perot filter elements can be used as a reflective wavelength filter rather than a transmissive one.

The wedged or stepped-shaped birefringence interference filters, the MOEMS device and the dispersive spectrometer disclosed herein can be made very compact and are particularly suitable for use in a handheld imaging system. Moreover, the filters can be configured to operate in two modes: imaging mode and spectroscopic mode. The tuning method can include line scan in a 1D spectrum. Thus, at a certain location X, the sample can be scanned as a function of Y and $\lambda$. The tuning speed can be as low as about 20 ms per wavelength or less than about 1 sec. per scanning line.

In this respect, a "compact" or "handheld" or "portable" version should be considered to comprise a self powered unit of the approximate size of a handheld calculator, cell phone, PDA or the like, namely of a size that can be carried conveniently in a pocket and deployed wholly by hand. Preferably the handheld device is about 36 $in^3$ or less (3×6×2 in) and can be as small as 9 $in^3$ (3×6×0.5 in) or less and the optical path measured from detector to the sample is about 2-4 inches.

In a handheld system using the tunable filter configurations disclosed herein may include a controller for controlling the tunable filter and the CCD. The controller may be in the form of a processor programmed by a software to communicate with the operator through a keypad and a display unit. The handheld system may also include a photon emission source, a polarization beam splitter, and a power source. The power source can be a battery. The photon emission source can include a laser (for Raman scattering), an LED (for white light reflectance application or fluorescence emissions), near infrared source, a fluorescent source or a combination thereof. The handheld device may also include one or more rejection filters for preventing the emission source from interfering with the LCTF and the detector.

Figure 11A:
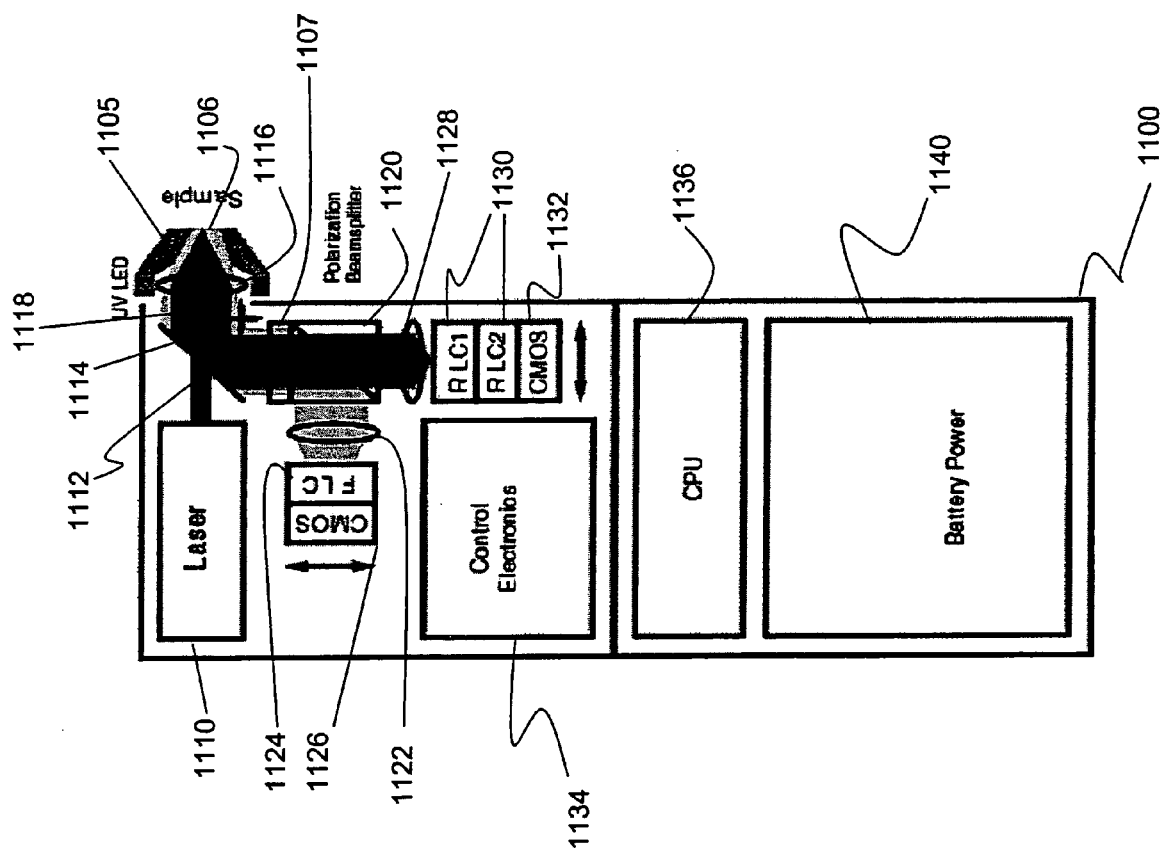
FIGS. 11A-11C are schematic illustrations of a handheld Chemical Imaging Threat Assessor detection device (CHITA) according to one embodiment of the invention.

FIG. 11A is a schematic illustration of a handheld Chemical Imaging Threat Assessor device according to one embodiment of the invention. Referring to the exemplary embodiment of FIG. 11A, the CHITA device includes miniaturized components efficiently packaged into a portable compact form for hand held operation. The unit includes illumination/excitations sources (laser source 1110 and light emitting diode source 1105), a lens and reflecting surface 1114, a scattered/emitted/reflected light conditioning filter 1107, a polarization beam splitter 1120, a combination of filter 1124 (e.g., a fluorescence liquid crystal tunable filter (FLC)) and detection system 1126 (e.g., CMOS or CCD) for wideband detection of sample region screening and selection, a second combination of filter 1130 (e.g., a Raman liquid crystal tunable filter (RLC1 and RLC2)) and detection subsystem 1132 (e.g., CMOS or CCD) for narrowband detection and identification, the control electronics 1134, processor unit 1136 and battery 1140. Imaging filter 1124 (FLC) is a fluorescence LCTF. Imaging filters 1130 (RLC1, RLC2) may be Raman LCTF. Conditioning filter 1107, which may be a "notch filter", is positioned before polarization beam splitter 1120 to block laser light from overwhelming the beam splitter 1120 and the subsequent detection systems 1124, 1130. Additionally, lenses 1122 and 1128 are positioned between beamsplitter 1120 and liquid crystals 1124 and 1130, respectively.

In the exemplary device of FIG. 11A, laser 1110 provides photonic beam 1112 which can be used for narrowband excitation and analysis including Raman analysis. The first filter/detection subsystem including emitting diodes (LEDs) can be used for screening purposes.

Figure 12:
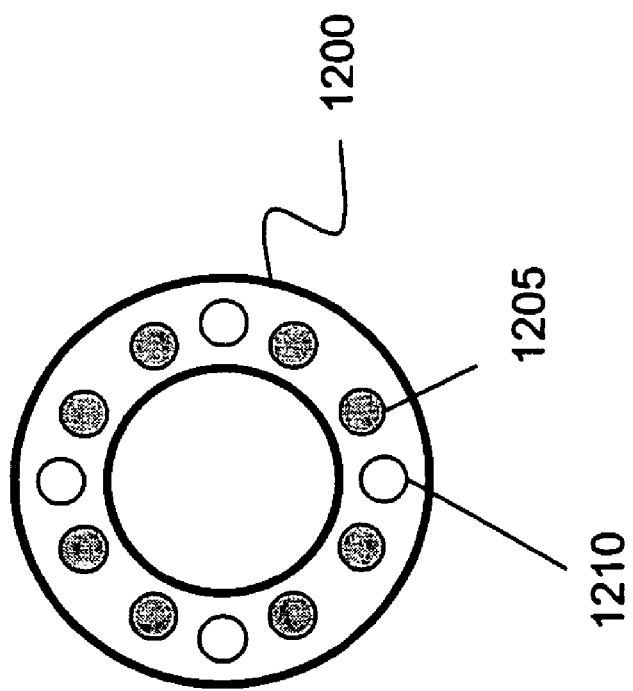
FIG. 12 is a secondary illumination source according to one embodiment of the disclosure.

FIG. 12 is a secondary illumination source according to one embodiment of the disclosure. In FIG. 12, the LED's are configured in a concentric ring 1200 normal to an axis that intersects the sample. In other words, they are formed as a ring 1200 and positioned in the vicinity of the sample (e.g., 1105 at FIG. 11A) to illuminate the sample with photons. The embodiment of FIG. 12 shows diode illuminating ring 1200 having LED's 1205 and 1210 which may illuminate the sample with different wavelengths. In other words, ring 1200 may include an array of similar of different light emitting diodes for irradiating the sample to enable sample detection and identification. In addition, the sample illumination may enhance laser detection and identification. LEDs 1205 and 1210 can be selected to operate in the visible, NIR or UV bands depending on the desired application. They may also be selected to consist of a mixture of different diodes selected for screening a combination of different chemical warfare or biological agents. The illumination source of FIG. 12 may also be configured to be a fluorescence source.

Referring again to FIG. 11A, the sample may be illuminated and analyzed substantially simultaneously or sequentially with laser from source 1110 and emitted photons from LED source 1105. Next, the scattered and emitted photons beam 1118 from the sample are collected by a lens 1116 and reflected by surface 1114 into the wavelength imaging filter. The reflecting surface 1114 can be configured to allow the laser light to pass thru while reflecting the scattered and emitted photon beam 1118. The illumination filter 1107 removes the wavelengths of the Raleigh scattered illuminating light that can swamp the detectors. The polarization beam splitter 1120 separates one polarization of the emitted and scattered light and allows it to be analyzed by the two different filters/detector subsystems shown to the left and below beam splitter 1120. Either CMOS (shown) or CCD detectors (1132, 1126) may register the wavelength selected/filters signals that are read and analyzed by the control module 1134 and an analyzer. The analyzer can be software stored on the CPU using data stored in the memory of the device. Alternatively, a processor can be programmed with a software to detect the chemical signature of the sample by comparing its spectrum with known spectrums stored in the CPU database.

Figure 11B:
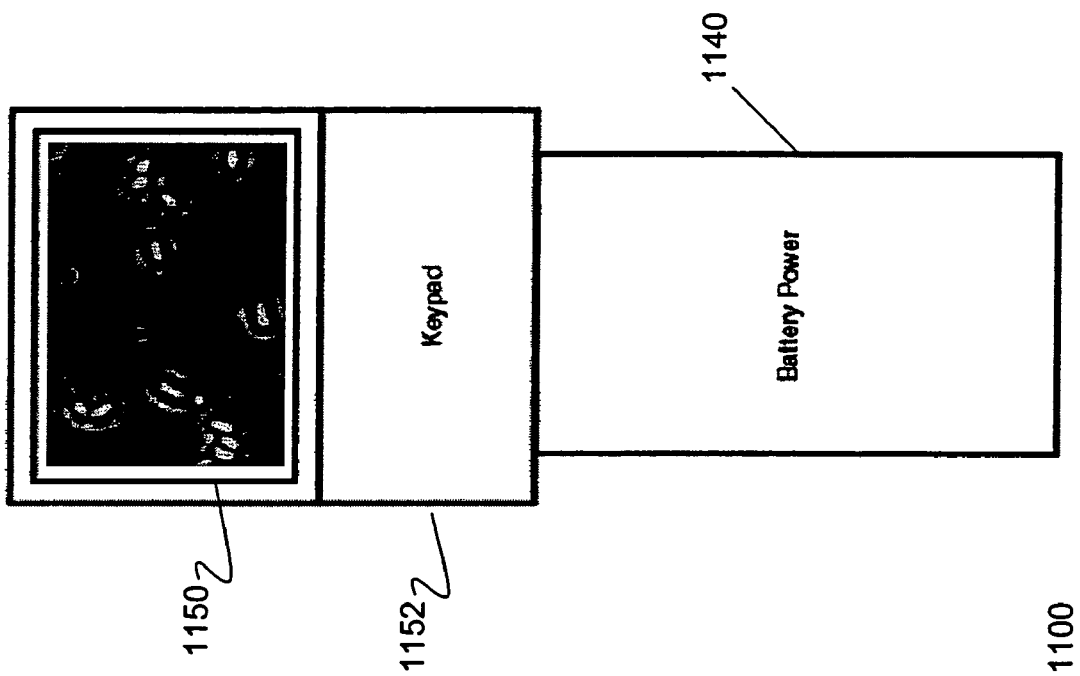

FIG. 11B shows a different side of the handheld device of FIG. 11A. Referring to FIG. 11B, device 1100 includes battery source 1140, keypad or other interface device 1152 and screen 1150. Screen 1150 may be configured for displaying the resulting images, or spectra and a bio-threat warning indication when such a threat is identified. The visual indicator can be complemented by an audio warning signal or other identification means. Keypad 1152 may be used for control and inputting data or for addressing commands to unit 1100. The device may also include one or more communication ports for electronically communicating with other electronic equipments such as a server, a printer or the like.

The Device 1100 can be used, for example, to detect and/or classify as to species, strains, and viability the following objects and/or pathogenic microorganisms, such as, for example, biological warfare agents and chemical warfare agents, as well as any growth medium associated therewith: Anthrax (*Bacillus anthracis*), protozoa, *cryptosporidia, Escherichia coli, Escherichia coli* 157, Plague (*Yersinia pestis*), Smallpox (variola major), Tularemia (*Francisella tularensis*), Brucellosis (*Brucella* species), *Clostridium pertringens*, Glanders (*Burkholderia mallei*), Melioidosis (*Berkholderia pseudomallei*), Psittacosis (*Chlamydia psittaci*), Q fever (*Coxiella burnetii*), Typhus fever (*Rickettsia prowazekii*), *Vibrio* (*Vibrio cholerae*), *Giardia, Candida albicans, Enterococcus faecalis, Staphylococcus epidermidis, Staphylococcus aureus, Enterobacter aerogenes, Corynebacterium diphtheriae, Pseudomonas aeruginosa, Acinetobacter calcoaceticus, Klebsiella pneumoniae, Serratia marcescens*, filoviruses (such as Ebola and Marburg viruses), naviruses (such as Lassa fever and Machupo viruses), alphaviruses (such as Venezuelan equine encephalitis, eastern equine encephalitis, and western equine encephalitis), Salmonella, and Shigella.

Device 1100 may be configured to illuminate or irradiate the sample and collect and analyze photons emitted or scatted by the sample. Analysis and identification can be accomplished as a function of the wavelengths emitted or scattered by the sample (i.e., the spectra of the sample). Thus, a spectra similar to that produced by a spectrometer can be obtained. In another embodiment, The principles disclosed herein are particularly advantageous in that device 1100 enables obtaining spatially resolved images as well as spectral identification of a sample simultaneously. In another embodiment, the disclosure relates to a portable system for obtaining a spatially accurate wavelength-resolved image of a sample having a first and a second spatial dimension. The portable system can include a photon emission source for sequentially illuminating a plurality of portions of said sample with a plurality of photons to produce photons scattered by the sample. The photon emission source can illuminate the sample along the first spatial dimension for each of plural predetermined positions of the second spatial dimension. The system may also include an optical lens for collecting the scattered photons to produce therefrom filtered photons, a dispersive spectrometer for determining a wavelength of ones of the filtered photons, a photon detector for receiving the filtered photons and obtaining therefrom plural spectra of said sample, and a processor for producing a two dimensional image of said sample from the plural spectra.

Figure 11C:
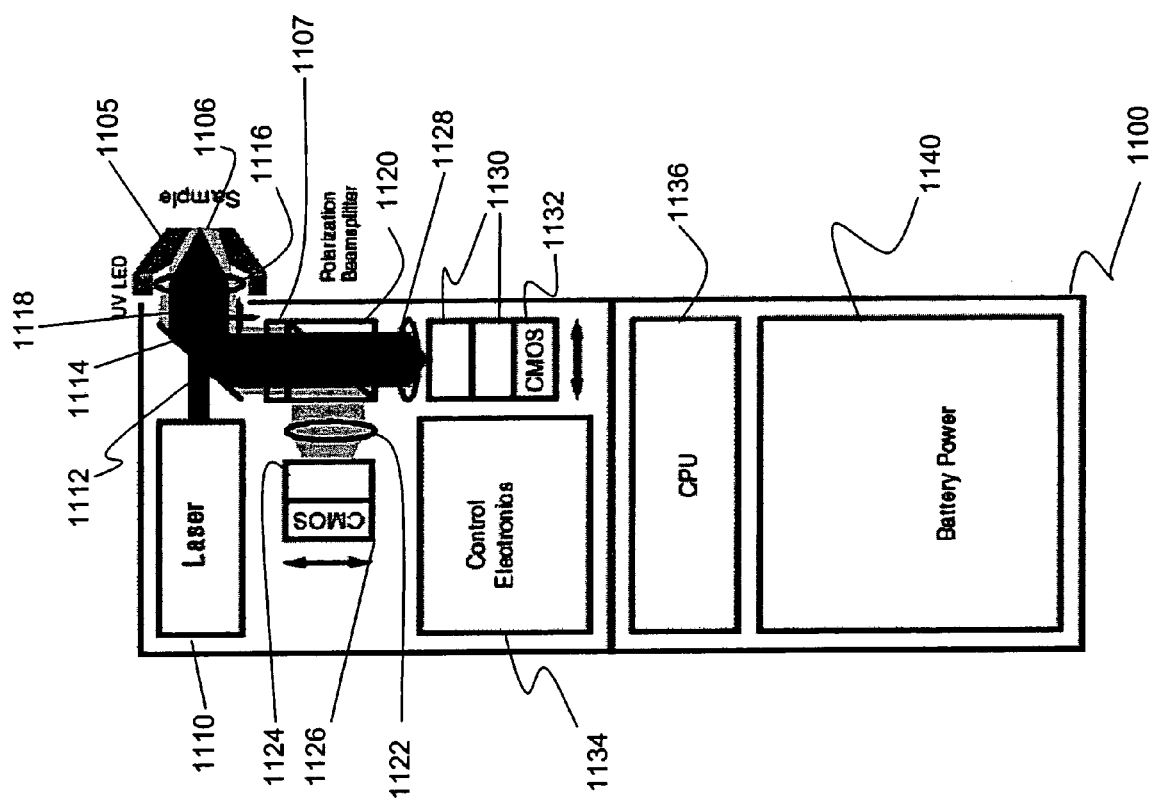

FIG. 11C is a schematic illustration of a handheld CHITA device according to another embodiment of the invention. Specifically, FIG. 11C shows an embodiment where filters 1124 and 1130 are each a dispersive spectrometer. In another embodiment, at least one of the filters 1124 or 1130 is replaced by a dispersive spectrometer.

In another embodiment, the device 1100 may be modified by the addition of a Fiber Array Spectral Transmitter ("FAST") system. The FAST system can provide faster real-time analysis for rapid detection, classification, identification, and visualization of, for example, hazardous agents, biological warfare agents, chemical warfare agents, and pathogenic microorganisms, as well as non-threatening objects, elements, and compounds. FAST technology can acquire a few to thousands of full spectral range, spatially resolved spectra simultaneously, This may be done by focusing a spectroscopic image onto a two-dimensional array of optical fibers that are drawn into a one-dimensional distal array with, for example, serpentine ordering. The one-dimensional fiber stack is coupled to an imaging spectrograph. Software is used to extract the spectral/spatial information that is embedded in a single CCD image frame. Fiber array spectroscopic imaging has been demonstrated in several applications including Raman chemical imaging analysis of micro-composites and biomaterials and time-resolved atomic emission chemical imaging of laser-induced plumes.

One of the fundamental advantages of this method over other spectroscopic methods is speed of analysis. A complete spectroscopic imaging data set can be acquired in the amount of time it takes to generate a single spectrum from a given material. FAST can be implemented with multiple detectors. Color-coded FAST spectroscopic images can be superimposed on other high-spatial resolution gray-scale images to provide significant insight into the morphology and chemistry of the sample.

The FAST system allows for massively parallel acquisition of full-spectral images. A FAST fiber bundle may feed optical information from is two-dimensional non-linear imaging end (which can be in any non-linear configuration, e.g., circular, square, rectangular, etc.) to its one-dimensional linear distal end. The distal end feeds the optical information into associated detector rows. The detector may be a CCD detector having a fixed number of rows with each row having a predetermined number of pixels. For example, in a 1024-width square detector, there will be 1024 pixels (related to, for example, 1024 spectral wavelengths) per each of the 1024 rows.

Figure 16:
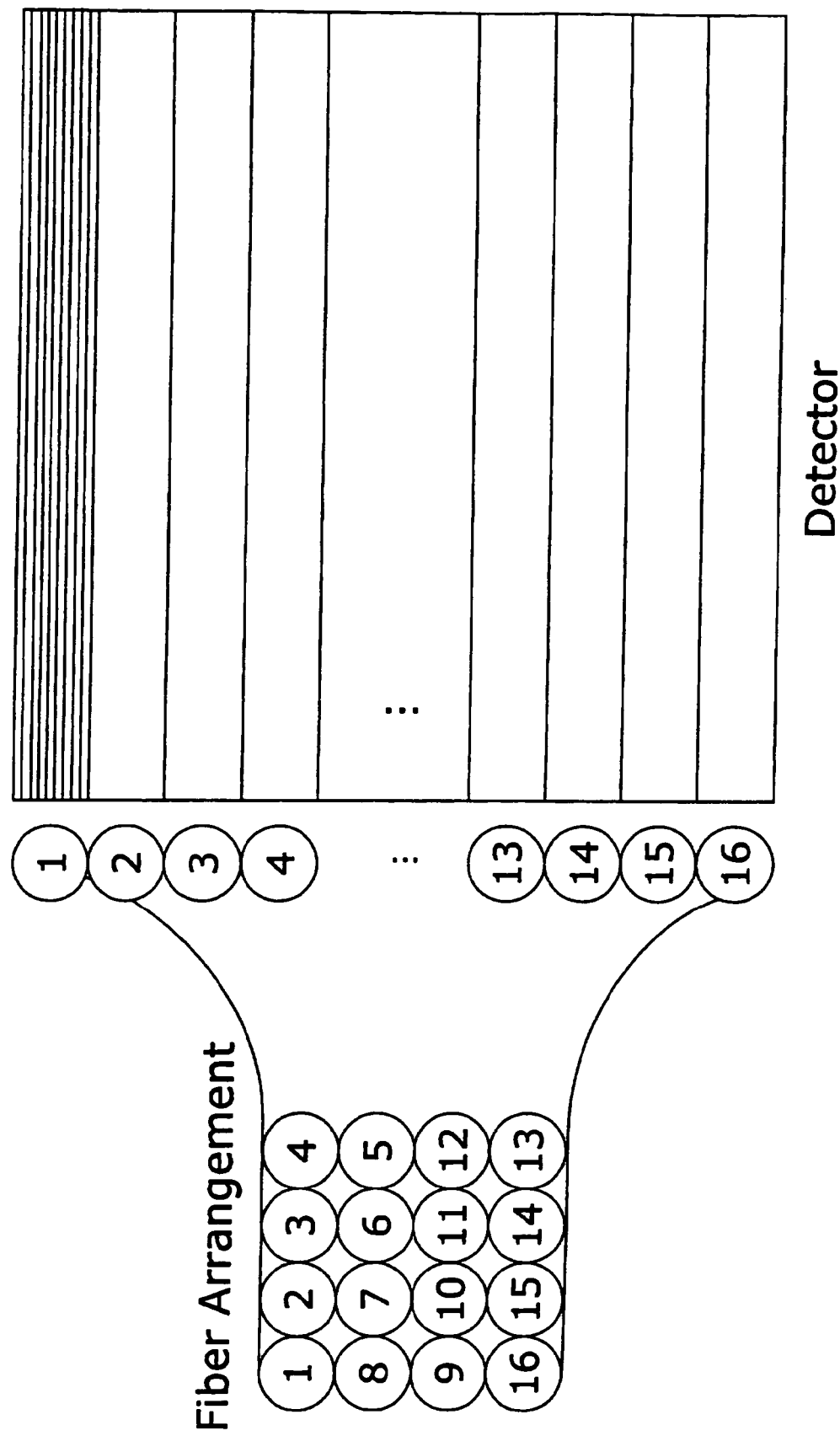
FIG. 16 is a simplified diagram of a FAST array showing the orientation of the fibers at the imaging end and the distal end.

The construction of the FAST array requires knowledge of the position of each fiber at both the imaging end and the distal end of the array as shown, for example, in the simplified diagram for FIG. 16 where a total of sixteen fibers are shown numbered in correspondence between the imaging end and the distal end of the fiber bundle. Each fiber collects light from a fixed position in the two-dimensional array (imaging end) and transmits this light onto a fixed position on the detector (through that fiber's distal end).

As shown in FIG. 16, each fiber may span more than one detector row, allowing higher resolution than one pixel per fiber in the reconstructed image. In fact, this super-resolution, combined with interpolation between fiber pixels (i.e., pixels in the detector associated with the respective fiber), achieves much higher spatial resolution than is otherwise possible. Thus, spatial calibration may involve not only the knowledge of fiber geometry (i.e., fiber correspondence) at the imaging end and the distal end, but also the knowledge of which detector rows are associated with a given fiber.

In yet another embodiment, a multipoint method and apparatus may be used in conjunction with the device 1100. This embodiment includes irradiating a sample with light, wherein the sample may be one or more of any of the types of samples mentioned herein, and assessing the Raman-shifted scattered radiation emanating from multiple points of the sample (e.g., two, four, five, ten, fifty, one hundred, or more). The points may be, for example, single pixels of an image of the viewing field or areas of the field represented in an image by multiple adjacent or grouped pixels. The shape (e.g., circular, annular, rectangular, etc.) of areas or pixels assessed as individual points is not critical. The multiple points have a defined geometric relationship with each other and the Raman-shifted scattered radiation is characteristic of the presence or absence of, for example, a hazardous agent in the sample. For example, Raman-shifted scattered radiation emanating from three, six, or ten points may be assessed. The points in the sample may be collinear, lie along two intersecting lines, be radially equidistant from a central point, or arranged otherwise, such as a random distribution not determinable from the image. Since the analysis or assessment of the Raman-shifted scattered radiation may only be performed on the particular points of the sample, and because the points of the sample may represent less than the entire field of view of the sample, the speed of analyzing the Raman-shifted scattered radiation is significantly increased. For example, the particular points of the sample may only represent 25% of the field of view, 5%, 1%, or even less.

The Raman-shifted scattered radiation may be transmitted through a spectrometer, a filter, or an interferometer prior to assessing the Raman-shifted scattered radiation for the presence or absence of a hazardous agent. The multipoint method and/or apparatus may be used in conjunction with a variety of Raman-shifted scattered radiation collection systems, such as a hand-held system, microscope, macroscope, endoscope, telescope, fiber optic array, or the previously-discussed FAST system.

An important aspect of the multipoint method and/or apparatus is the discovery that the presence or absence of a hazardous agent in a sample can be estimated accurately by assessing Raman scattering from multiple points in the sample. Sampling of multiple points in a relatively large field of view can yield compositional information about the sample in the field without the need either to collect extensive data from all points in the field or to average the spectral information of the entire field. The multipoint imaging methods described can therefore be used to determine both the composition of a sample as well as the degree of homogeneity within the sample. If desired, a more detailed Raman analysis of one or more of the areas and/or samples in which the multipoint analysis indicates the presence of a hazardous agent may be undertaken.

The area corresponding to each point of a multipoint analysis can be selected or generated in a variety of known ways. By way of example, a confocal mask or diffracting optical element placed in the illumination or collection optical path can limit illumination of collection to certain portions of the sample having a defined geometric relationship.

In addition to Raman spectra, other spectroscopic measurements (e.g., absorbance, fluorescence, refraction) can be performed to assess one or more of the points sampled by Raman spectroscopy. This information can be used alone or as a supplement to the Raman spectral information to further characterize the portions of the sample corresponding to the individually analyzed points. This information can also be used in place of Raman spectral information. Raman spectroscopy often provides more information regarding the identity of imaged materials than many other forms of spectroscopic analysis, so inclusion of Raman spectroscopy in the methods is preferred. Additional spectroscopic information (including absorbance spectral information or image-based optical information such as the shapes of objects in the field of view) can help select a field of interest for Raman analysis, confirm the Raman spectroscopic analysis for a point, or both.

Spectroscopic analysis of multiple points in a field of view (i.e., multipoint analysis) allows high quality spectral sensing and analysis without the need to perform spectral imaging at every picture element (pixel) of an image. Optical imaging can be performed on the sample (e.g., simultaneously or separately) and the optical image can be combined with selected Raman spectrum information to define and locate regions of interest. Rapidly obtaining spectra from sufficient different locations of this region of interest at one time allows highly efficient and accurate spectral analysis and the identification of materials such as hazardous agents in samples. Furthermore, identification of a region of interest in a sample or in a viewing field can be used as a signal that more detailed Raman scattering (or other) analysis of that portion of the sample or viewing field should be performed.

The multipoint method can be performed much more rapidly than chemical imaging methods, because far less raw data collection is involved. By selecting multipoint areas that are on a scale corresponding to an anticipated analyte, averaging of spectra data across the relatively limited area of each point can capture the unique spectra of the analyte. Because the multipoint area can correspond to many pixels in a full chemical image, the spectral sensing points can also improve the signal-to-noise ratio of the spectrum of each area. If the non-homogeneity of a sample can be anticipated, then the area of suitable points for Raman scattering analysis can be selected or determined based on the Raman spectra of the anticipated components and their relative amounts. point size (i.e., the size of the area sampled in each of multiple points) can thereby be selected such that Raman characteristics of the analyte of interest (e.g., a hazardous agent) will be distinguishable from other components and anticipated background Raman scattering. The multipoint method thus can be performed with greater speed and less noise or with a greater spatial resolution and lower detection limit than the widefield chemical imaging method.

Figure 17:
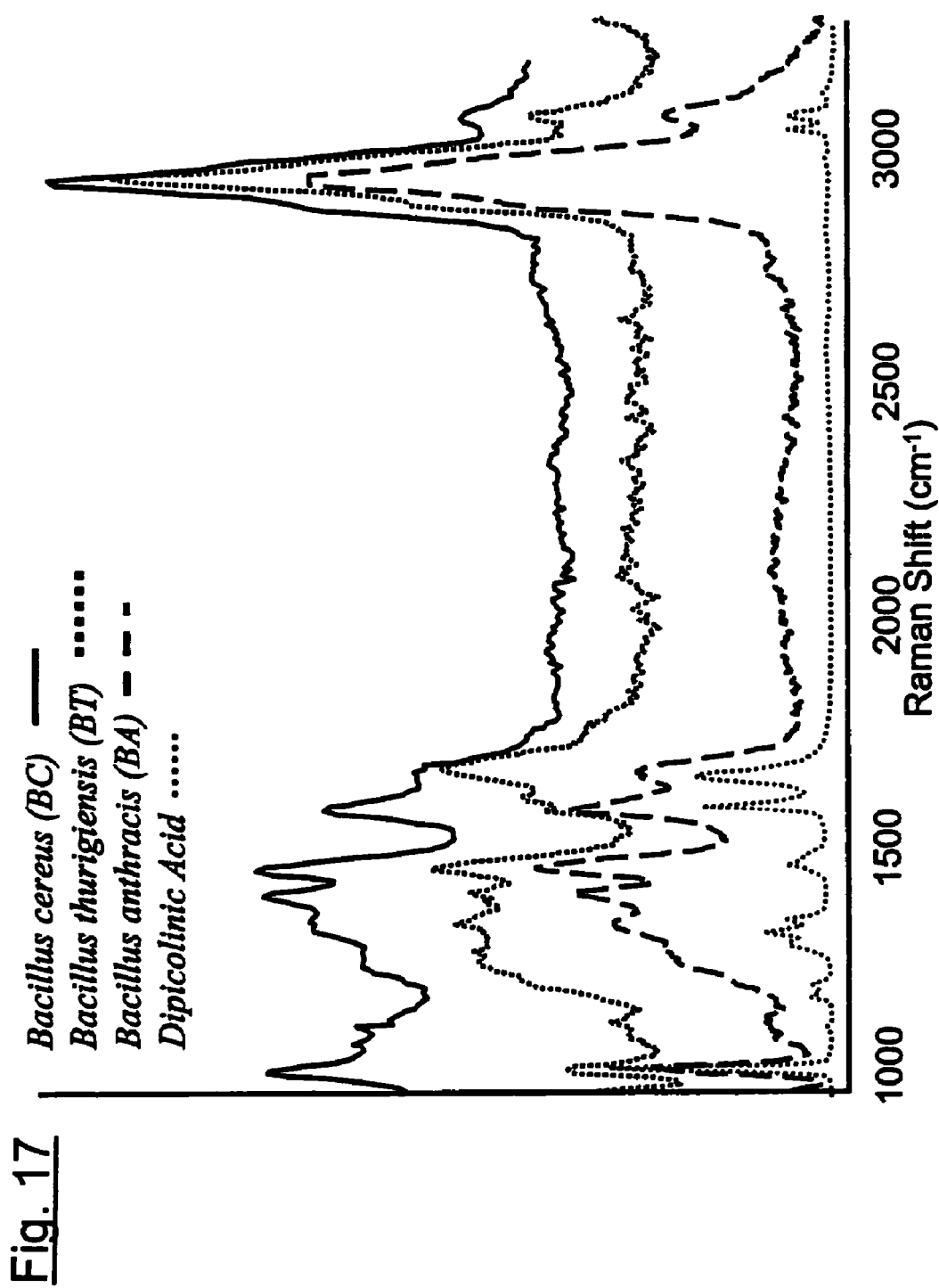
FIG. 17 is a graph of the Raman spectra of three Bacillus species and dipicolinic acid.

In FIG. 17, the spectra shown include a Raman spectrum corresponding to *B. anthracis*. The differences which are evident between the spectrum of *B. anthracis* and the spectra of the other *Bacillus* species demonstrate that *B. anthracis* can be differentiated from those species in a sample containing all three agents. This is performed by analyzing the Raman spectra of individual points in the sample and assigning an identity to the point, based on similarity to the known spectra. Any of a variety of known methods can be used to correlate the spectrum obtained at any particular point with reference spectra. By way of example, standard spectral library comparison methods can be used or the spectral unmixing methods described in U.S. patent application Ser. No. 10/812,233, filed 29 Mar. 2004, can be used. Sampling multiple points in an image allows variations in the spectra to be observed and distinctions to be made as to components present in the various portions of the sample corresponding to the points. Acquiring data at every position and analyzing the spectra at every point in an image would require significantly greater time. Multipoint spectral sensing simplifies this by focusing on specific spatial locations within the sample.

The area of points sampled can be as small as the resolution limits of the equipment used (i.e., one pixel). Preferably, multiple pixels are included in the point, so that spectral averaging methods can be used to reduce noise in the detected signal. The size of the area of each point should preferably not be greater than a small multiple of the anticipated size of the particle size of the agent to be detected. For example, in one embodiment, if the presence or absence of bacterial spores are to be analyzed, then the point size should not be greater than 2, 3, 5, 10, or 25 times the cross-sectional area of a single spore. By way of example, bacteria and their spores have characteristic dimensions that are typically on the order of one to several micrometers, viruses have characteristic dimensions that are on the orde4r of tens of nanometers, and eukaryotic cells have characteristic dimensions that are on the order of ten to hundreds of micrometers. The characteristic dimensions of chemical agents, including biological toxins, depend on their agglomeration, crystallization, or other associative characteristics. The characteristic size of analytes can also depend on sample components other than the analyte itself (e.g., binding or agglomerating agents).

When the area of a sample corresponding to a point at which a Raman spectrum is assessed is much larger than a characteristic dimension of an analyte or an analyte-containing particle, the methods described herein can still be employed. In that instance, the results obtained using the method will be indicative of the presence of the analyte in a region of the sample, rather than pinpointing the location of a discrete particle of the analyte. Such regions of the sample can be subjected to further analysis (e.g., finer multipoint Raman analysis or Raman chemical imaging analysis) if desired. A skilled artisan will understand how to select appropriate point sizes based on the desired analyte in view of this disclosure.

The areas corresponding to individual points in a sample need not be equal for all points in the same field of view. For example, smaller point sizes can be used in an area of the field in which finer spatial resolution is desired. Likewise, a field of view can be analyzed separately using multiple equal point sizes. By way of example, a field of view can be first analyzed at several relatively large points and, if the analyte is recognized at one of the points, a portion of the sample corresponding to that point (e.g., the quadrant of the sample that includes the point, all areas within a certain distance of the point, or the entire sample, if desired) can be re-analyzed using smaller point sizes. Multiple rounds of such analysis and point size reduction can result in images having very finely-resolved portions of interest and more crudely-resolved areas of lesser or no interest, while minimizing information processing requirements. Variable magnification or an optical zoom can be used to vary the area of the points sampled. In this way, the area corresponding to a sampled point can be matched with the size of pixels of the detector. The area of illuminated points can be controlled in the same way (i.e., conjunction with a grid aperture or other beam-shaping device).

Some considerations that can affect the size and shape selected for areas corresponding to individual points include the following. The size and shape can be selected to correspond to the geometry of the device used for illuminating the sample or the geometry of detector elements in the detector. The size of the hazardous agent to be detected can influence the size, shape, and spacing of the points. For instance, the area of the point can be selected so that a desired amount of hazardous agent (e.g., a single microorganism) in the point area will yield a detectable signal even if the remainder of the area is free of the hazardous agent. The minimum limit of detection desired for the hazardous agent can be determined by the proportion of the field of view that would be covered by the hazardous agent at that level, so the pattern or number of points sampled can be selected with that hazardous density in mind.

Multipoint spectral sensing can be applied separately or combined with methods of Raman, fluorescence, UV/visible absorption/reflectance, and near infrared ("NIR") absorption/ reflectance spectroscopies. Contrast can be generated in images by superimposing, adding, or otherwise combining spectral information obtained by these spectroscopic methods. Because a spectrum is generated for each point assessed in a multipoint analysis, chemometric analysis tools such as correlation analysis, principal component analysis ("PCA"), and factor rotation, including multivariate curve resolution ("MCR"), can be applied to the image data to extract pertinent information that might be less obvious by analyzing only ordinary univariate measures.

Furthermore, regions of a sample suitable for multipoint Raman scattering analysis can be identified by first using other optical or spectroscopic methods. By way of example, in a method for assessing the presence of a pathogenic bacterium, optical microscopy can be used to identify regions of a sample that contain entities having the size and/or shape of bacteria. Fluorescence analysis can be used to assess whether the entities identified by optical microscopy appear to be of biological origin (i.e., by exhibiting fluorescence characteristic of bacteria). For portions of the sample containing entities which appear to have the size and/or shape of bacteria and exhibit apparently biotic fluorescence, Raman scattering analysis can be performed at multiple points within that portion, as described herein. Further by way o example, NIR imaging can be used to identify a suspicious portion of a parcel that is not transparent to visible light, and to perform multipoint Raman scattering analysis on that suspicious portion.

By way of example, the intensity of radiation assessed at one Raman shift value can be superimposed on a black-andwhite optical image of the sample using intensity of red color corresponding to intensity of the Raman-shifted radiation at a particular Raman shift value, the intensity of radiation assessed at a second Raman shift value can be superimposed on the image using intensity of blue color corresponding to intensity of the second Raman-shifted radiation, and the intensity of fluorescence radiation assessed at one fluorescent wavelength can be superimposed on the image using intensity of green color corresponding to intensity of the fluorescent radiation. Further by way of example, if the characteristics of a portion of the image are within the limits or predetermined criteria for detecting the presence of a hazardous agent, the portion of the image for which the characteristics meet those criteria can be made to switch on and off to otherwise indicate the presence of the detected agent.

Depending on the materials and the spectroscopic method(s) used, depth-related information can also be obtained by using different excitation wavelengths or by capturing spectroscopic images at incremental planes of focus. Thus, depending on the penetrating ability of illumination and detected wavelengths, the contents of objects (e.g., vials, envelopes, or suitcases) can be assessed using these methods.

A spatial resolving power of approximately 250 nanometers has been demonstrated for Raman spectroscopic imaging using visible laser wavelengths and commercially available devices. This is almost two orders of magnitude better than infrared imaging, which is typically limited to a resolution not better than 20 micrometers, owing to diffraction for example. Thus, multipoint size definition performed using Raman spectroscopy can be higher than other spectroscopic methods and Raman methods can be used to differentiate spectral features of small objects. Simplified designs of detectors (i.e., relative to chemical imaging devices) are possible since spectroscopic imaging and the assembly of a spectral image is not necessary in this approach.

An advantage of using NIR radiation in multipoint spectral sensing is that it penetrates more deeply than visible light so as to enable one to probe inside or paper or plastic envelops or plastic or glass containers, for example, to detect a hazardous agent in such a container. Any container that does not totally absorb the incident radiation can be examined using the NIR multipoint spectral sensing approach.

In another embodiment, the device 1100 is used in conjunction with both the multipoint method and FAST. The high numbers of optical fibers required for FAST imaging applications place extraordinary demands on the imaging spectrograph which the multipoint method addresses. Instead of having millions of pixels, multipoint analysis can utilize larger diameter fibers in bundles containing tens to hundreds of fibers. In the multipoint method of spectral sensing and analysis, complete spectral imaging (which would require at least thousands of adjacent pixels to create a physical image) is not required. Instead, spectral sensing performed at tens to hundreds of points simultaneously can rapidly (on the order of seconds, for example) provide high quality spatially resolved spectra from a wide variety of points on the sample needed for analysis and identification. Thus, even if the precise geometric arrangement of the points analyzed in the field of view is not known, the points nonetheless have a defined geometrical arrangement which can span a sample or a field of view. The analyzed points are informative regarding the presence and, if present, the amount of hazardous agent of interest in a sample.

An advantage of this method over other current point spectroscopic detection methods is speed of analysis. A complete spectroscopic multipoint data set can be acquired in the amount of time it takes to generate a single spectrum from a given material. Even with limited pixel definition, superimposing color-coded multipoint spectral data obtained from known areas of a field of view on high-spatial resolution gray-scale images can provide significant insight into the morphology and chemistry of materials.

Figure 13:
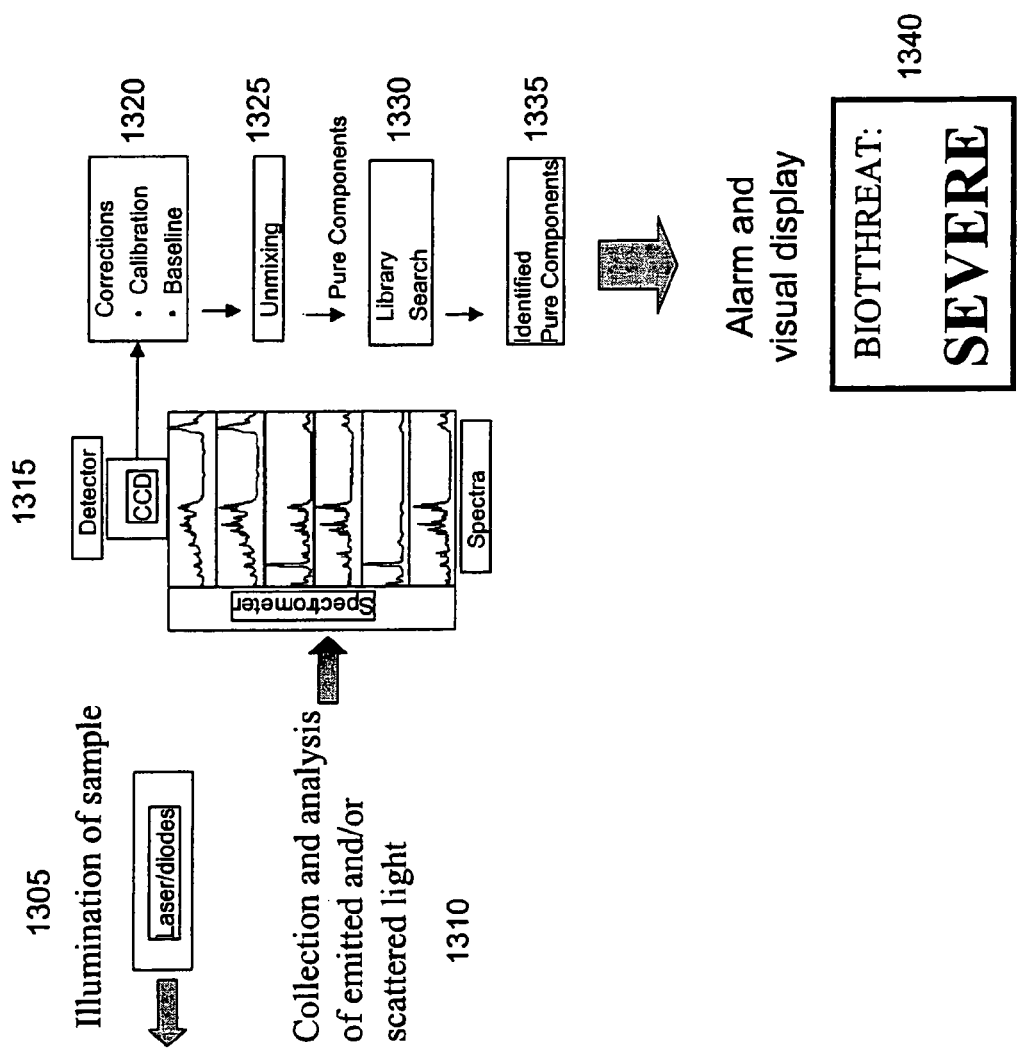
FIG. 13 schematically illustrates the operation of an exemplary detection device.

FIG. 13 schematically illustrates the operation of an exemplary CHITA device. As shown, a sample is first illuminated 1305 by one or more photon sources (e.g., LED 1105 and laser 1110 in FIG. 11A). The next step, 1310, is the collection and analysis of the emitted and/or scattered photons from the sample. Once the wavelength and spatially resolved data/information is obtained, in step 1315 the data is directed to a CMOS or CCD detector. This data is then processed by the CPU to perform various corrections to the raw data for detailed analysis. The correction analysis may include calibration and baseline corrections 1320, unmixing of the different spectral features 1325 (such as those disclosed in U.S. patent application Ser. No. 10/812,233 and incorporated herein for background information), searching a local database for potential spectral matches 1330 and identification of the sample 1335. The analysis may be repeated for different spatial locations on a sample. The spectral data can be stored in the CPU 1136 or compared with baseline data stored in an onboard memory. The exemplary processing steps enable detected and identification of compounds classified as biothreat or chemical threat 1340.

According to the foregoing embodiments, pixilized or otherwise incremental parts of the tunable filter are independently tunable, and can be tuned wholly independently or in a coordinated way to filter selectively for the wavelengths to be applied to the data capture devices at different points in the image or data capture field (e.g., an X-Y field of photosensors or a line of photosensors in a pushbroom configuration). In the stepped-thickness retarder embodiments, for example, a succession of pixel areas or bands are tunable together, so as to provide a succession of incremental areas (at each step) tuned to successive wavelengths that differ according to the difference in retarder thickness from one step to the next. Similarly, in a wedge shaped retarder embodiment, tuning over the wedge selects for a succession of wavelengths in a range, the wavelength varying continuously across the surface at which the retarder thickness varies between its greatest and least thickness. In a wholly pixilized filter, the individual pixels could be tuned to wavelengths that are different from the tuned wavelengths of other potentially-adjacent pixels.

It is an aspect of the invention, therefore, that different positions on the tunable filter area are tuned to different wavelengths at the same time. This is a departure from the expected technique of collecting wavelength specific light amplitude data over the entire filter area at one wavelength, and then proceeding to collect a next set of data at a next wavelength until the entire spectrum is collected for each pixel position. However, the invention provides improved speed and versatility by foregoing the need to collect the full spectrum (all the wavelengths) for the full tunable area before an analysis of the data can be accomplished.

It is possible using the independent or stepwise tuning capability of the invention to collect full spectrum information at each pixel position. In that case, it is necessary to manage the data collection so as to keep track of the tuned wavelength for which each light amplitude measurement applies.

According to the invention, it is also possible to collect a series of different wavelength measurements from a sample at one time. This can be accomplished, for example, by defocusing or otherwise applying the reflected light of an image diffusely over all the tunable positions in an array (e.g., a wedge or series of steps of different retarder thickness) and accumulating wavelength data from the whole sample in a manner similar to the manner in which light from a slit might be applied to a spectrograph using a prism or grating. That is, the wedge or stepped or pixilized retarder arrangements can be operated as to collect an average spectrum for a whole sample image. The same arrangements also can be used to collect an average spectrum over a selected part of an image.

In one example, the tunable filter is controlled by a processor such as processor 1136 in FIG. 11A, and the processor also controls successive data acquisition modes. As one step, focused fluorescence imaging is used to collect an image of the sample. One or more particular areas of the image can be distinguished by detection of features of interest, e.g., by contrast at some characteristic wavelength. In a next mode, the area of interest, or optionally diffuse light from the entire sample, is examined for particular wavelength relationships, optionally using very narrow bandwidth (but slow) Raman imaging. Inasmuch as it is not necessary to collect a full spectrum of data for every pixel or other tunable increment, the sample analysis can be substantially faster than would be possible otherwise.

The dispersed wavelength capabilities of the wedge shaped, step shaped, and separately tunable retarders of the foregoing embodiments thus can accomplish spectral analysis by collecting full spectra for pixels, or spectral analysis by collecting an average spectrum of the image, or differential wavelength analysis wherein adjacent or other areas of the image are selective tuned to different wavelengths.

Accordingly, in one embodiment, a handheld detection system, for threat detection or other applications, can be configured and controllably operated to use a birefringent spectrally "agile" interference filter element, namely an element that is tunable selectively to one or to a plurality of different wavelengths at a given time, to accomplish fluorescence imaging, reflectance image collection, Raman image and Raman image-average spectrum collection and analysis. Any one or a combination of the filter layouts disclosed herein can be used in the handheld device. For example, referring to FIG. 11A, RLC1 and RLC2 (Raman liquid crystal) may be a wedged filter or a tunable filter as described above. Similarly, FLC 1124 may include a dispersive filter as disclosed above.

Figure 14:
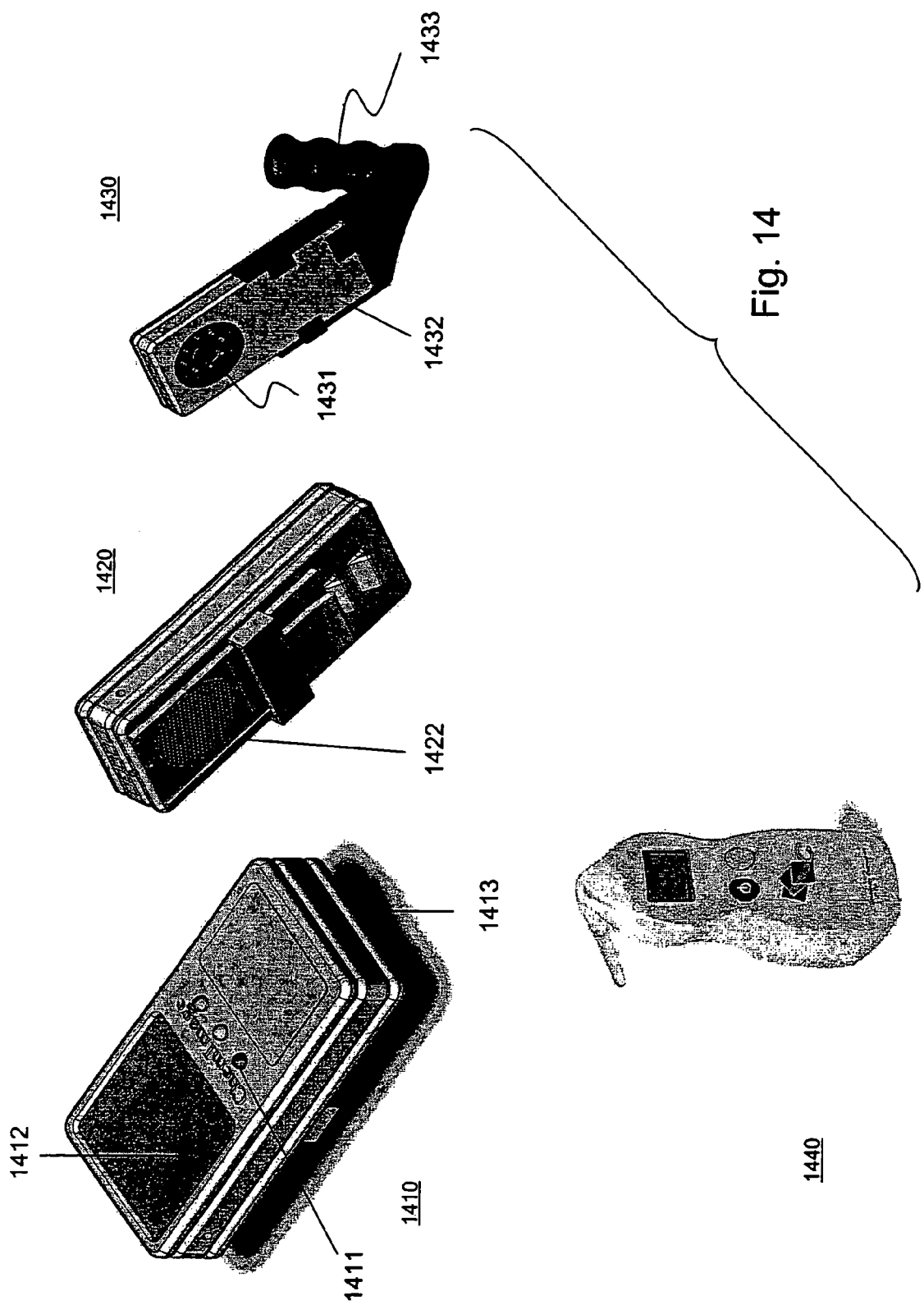
FIG. 14 provides exemplary packaging options according to one embodiment of the disclosure.

FIG. 14 provides exemplary packaging options according to one embodiment of the disclosure. Referring to FIG. 14, device 1410 illustrates a handheld device suitable similar to that shown in FIGS. 11A and 11B. The handheld device 1410 includes screen 1412 for displaying various information with the operator, alarm signals 1411 and communication port 1413 enabling data communication with other electronic devices. Device 1400 can be used for bio-threat detection as it can display images as well as text. This unit can be configured to identify a large range of bio-threat material determined by the size of the onboard library of bio-threat signatures contained in its memory. It may also be configured for remote communication with a host station using a wireless link to report important findings or update its library.

Handheld air monitor 1420 is shown to include port 1422. Finally, handheld surface detection device 1430 is shown to have handle 1433, LED source 1431 having a ring formation and body 1432. While not shown, handheld surface detection device may also include a display, a keypad and one or more communication ports. The devices shown in FIGS. 11A, 11B and 14 illustrate that the embodiments disclosed herein can be assembled and packaged in a handheld device for field application. It can be readily seen that such devices are compact and while having a small optical path (measured between the sample and the detector) can be as efficient as the table-top units. Devices 1420 and 1430 are particularly suitable for air monitoring or surface detection of bio-threats, respectively. Handheld detector 1430 can be used for measuring bio-threats on the clothing or exposed body parts, which can be particularly useful on the battlefield or in a civil setting While the exemplary embodiment of FIG. 14 are discussed in relation with bio-threat detection, such device are equally suited for chemical warfare agent detection or hazardous material monitoring. Another application of detection device 1410 may include detection and monitoring of chemicals in human body for medical purposes. A consumer device using the principles disclosed herein can also be configured for conducting self-diagnostic tests for identifying agents such as glucose, cholesterol, urea, hemoglobin and alcohol.

Finally, handheld device 1440 represents an exemplary representation of a lower cost, consumer oriented device with simplified operating controls and menu driven input similar to a cellular telephone. This unit can be programmed to detect a certain chemicals depending upon its intended application.

An alternate embodiment for the handheld detector involves the use of a Raman micro-spectrometer as the dispersing filter for Raman scattering. To achieve the small size required for a portable handheld detector, the micro Raman sensor component can be constructed from semiconductor lithographic materials such as PMMA and x-ray lithography processes known to those skilled in the art of semiconductor processing. Fabrication involves exposure of polymethyl methacrylate (PMMA) fitted with an X-ray mask to synchrotron radiation. Here the exposures can be performed using an in-plane micro-optical systems known to those skilled in the art and fabricated in batch mode via deep x-ray lithography. Subsequent steps may involve development of the exposed PMMA and removal of same, electroformation in the PMMA cavity, planarization of the combined materials, removal of the protected PMMA, and finally release of the electroformed component. This process produces a PMMA grating which can be used as the miniature wavelength dispersive element for the CHITA handheld detector. Following the art for construction of dispersive spectrometers, this grating is inserted into the optical path so as to spread the filtered wavelengths over the detector surface to detect the range of wavelengths coming from the sample.

Figure 15:
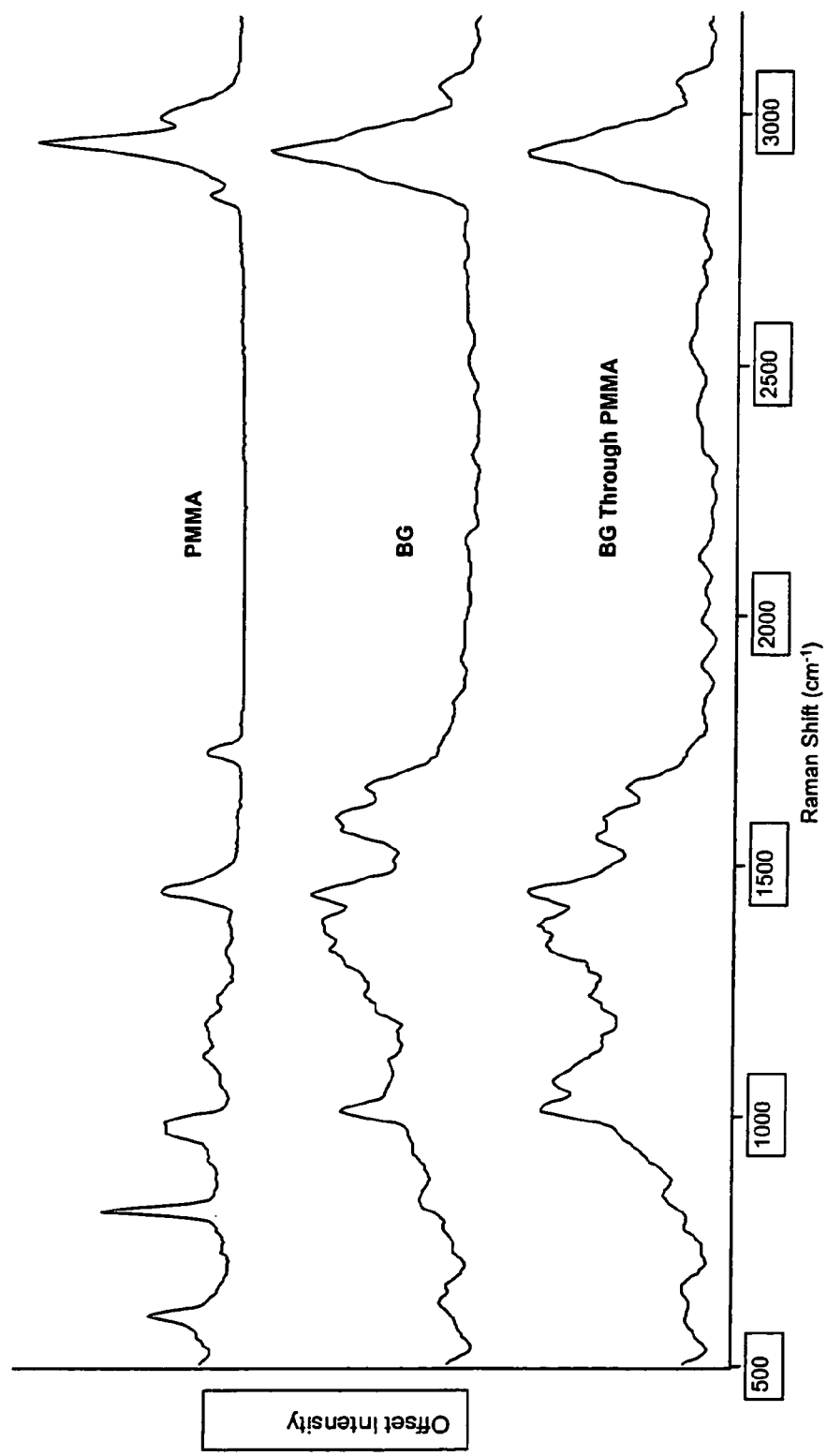
FIG. 15 shows dispersive Raman spectroscopy of a sample through PMMA.

A feature of the ultra compact filter is that the optical properties and Raman features inherent to PMMA do not substantially degrade the Raman detection of bio-threat agents. FIG. 15 shows the Raman spectrum of PMMA collected using high performance microscope glass optics. FIG. 15 also shows the Raman spectrum of a species of Anthrax (BG) collected with the same optics. Finally, FIG. 15 shows a Raman spectrum of BG after introducing a thin plate of PMMA into the laser illumination and collection optical paths. So long as the PMMA is located in an optical region where the light rays are parallel, it does not introduce significant background into the measured spectrum. That is, PMMA is illumination optical path does not prevent collection of BG Raman spectrum. The contribution to the Raman spectrum attributable to PMMA can be also be used as an internal calibrant (intensity and wavelength) which can assist automated correction of instrument response and overall improved performance of a fielded system. Instrument calibration enables compensation of instrument variation including laser line drift and quantitative analysis.

The following Table shows non-exclusive and exemplary specifications for an embodiment of the compact imaging spectrometer.

| Performance Parameter | Specification |
| --- | --- |
| Laser excitation wavelength and bandwidth: | 532 nm; <0.2 nm |
| Imaging aperture: | 0.5" or larger |
| Field of view (angular incidence): | +/−3 degrees |
| Free spectral range: | 500-750 nm |
| Usable Raman range: | 350-3,200 cm$^{-1}$ |
| Resolution: | 0.25 nm FWHM @ 500 nm, <10 cm$^{-1}$ |
| Off-peak rejection: | 10,000:1 total energy |
| Transmission: | min 30% |

Although the disclosure is described using illustrative embodiments provided herein, it should be understood that the principles of the disclosure are not limited thereto and may include modification thereto and permutations thereof.

What is claimed is:

1. A method for detecting an agent in a sample comprising the steps of:
   (a) illuminating a sample with photons emanating from a device to thereby produce Raman-scattered photons from the sample;
   (b) forming a spatially-accurate wavelength resolved image of at least a portion of the sample using the Raman-scattered photons; and
   (c) analyzing the spatially-accurate wavelength resolved image using the device to detect patterns characteristic of the agent.

2. The method of claim 1 wherein the agent is a hazardous substance.

3. The method of claim 2 wherein the agent is anthrax.

4. The method of claim 2 wherein the agent is a pathogenic microorganism.

5. The method of claim 1 wherein the pathogenic microorganism is selected form the group consisting of: Anthrax (*Bacillus anthracis*), protozoa, cryptosporidia, *Escherichia coli*, *Escherichia coli* 157, Plague (*Yersinia pestis*), Smallpox (variola major), Tularemia (*Francisella tularensis*), Brucellosis (*Brucella* species), *Clostridium pertringens*, Glanders (*Burkholderia mallei*), Melioidosis (*Berkholderia pseudomallei*), Psittacosis (*Chlamydia psittaci*), Q fever (*Coxiella burnetii*), Typhus fever (*Rickettsia prowazekii*), *Vibrio* (*Vibrio cholerae*), Giardia, *Candida albicans, Enterococcus faecalis, Staphylococcus epidermidis, Staphylococcus aureus, Enterobacter aerogenes, Corynebacterium diphtheriae, Pseudomonas aeruginosa, Acinetobacter calcoaceticus, Klebsiella pneumoniae, Serratia marcescens*, filoviruses (such as Ebola and Marburg viruses), naviruses (such as Lassa fever and Machupo viruses), alphaviruses (such as Venezuelan equine encephalitis, eastern equine encephalitis, and western equine encephalitis), Salmonella, and Shigella.

6. The method of claim 1 wherein the illuminating photons are in the visible spectrum.

7. The method of claim 1 wherein the illuminating photons are in the ultraviolet spectrum.

8. The method of claim 1 wherein the illuminating photons are in the infrared spectrum.

9. The method of claim 1 further comprising the step of:
   (d) determining a strain of the agent from the analysis of the image.

10. The method of claim 1 further comprising the step of:
    (d) determining the viability of the agent from the analysis of the image.

11. The method of claim 1 further comprising the step of:
    (d) determining a growth medium of the agent from the analysis of the image.

12. The method of claim 1 wherein the device is a hand held device.

13. A system for detecting an agent in a sample comprising:
    (a) a device comprising a photon source for illuminating a sample with photons to thereby produce Raman-scattered photons from the sample;
    (b) means for forming a spatially-accurate wavelength resolved image of at least a portion of the sample using the Raman-scattered photons; and
    (d) means for analyzing the spatially-accurate wavelength resolved image using the device to detect patterns characteristic of the agent.

14. The system of claim 13 wherein the agent is a hazardous substance.

15. The system of claim 14 wherein the agent is anthrax.

16. The system of claim 14 wherein the agent is a pathogenic microorganism.

17. The system of claim 13 wherein the pathogenic microorganism is selected form the group consisting of: Anthrax (*Bacillus anthracis*), protozoa, cryptosporidia, *Escherichia coli*, *Escherichia coli* 157, Plague (*Yersinia pestis*), Smallpox (variola major), Tularemia (*Francisella tularensis*), Brucellosis (*Brucella* species), *Clostridium pertringens*, Glanders (*Burkholderia mallei*), Melioidosis (*Berkholderia pseudomallei*), Psittacosis (*Chlamydia psittaci*), Q fever (*Coxiella burnetii*), Typhus fever (*Rickettsia prowazekii*), *Vibrio* (*Vibrio cholerae*), Giardia, *Candida albicans, Enterococcus faecalis, Staphylococcus epidermidis, Staphylococcus aureus, Enterobacter aerogenes, Corynebacterium diphtheriae, Pseudomonas aeruginosa, Acinetobacter calcoaceticus, Klebsiella pneumoniae, Serratia marcescens*, filoviruses (such as Ebola and Marburg viruses), naviruses (such as Lassa fever and Machupo viruses), alphaviruses (such as Venezuelan equine encephalitis, eastern equine encephalitis, and western equine encephalitis), Salmonella, and Shigella.

18. The system of claim 13 wherein the illuminating photons ate in the visible spectrum.

19. The system of claim 13 wherein the illuminating photons ate in the ultraviolet spectrum.

20. The system of claim 13 wherein the illuminating photons are in the infrared spectrum.

21. The system of claim 13 further comprising:
    (d) means for determining a strain of the agent from the analysis of the image.

22. The system of claim 13 further comprising:
    (d) means for determining the viability of the agent from the analysis of the image.

23. The system of claim 13 further comprising:
    (d) means for determining a growth medium of the agent from the analysis of the image.

24. The system of claim 13 wherein the device is a hand held device.

25. The system of claim 13 further comprising a filter.

26. The system of claim 25 wherein the filter is a tunable filter.

27. The system of claim 26 wherein the tunable filter is a liquid crystal tunable filter.

28. The system of claim 27 wherein the liquid crystal tunable filter is selected from the group consisting of: Lyot liquid crystal tunable filter, Evans Split-Element liquid crystal tunable filter, Solc liquid crystal tunable filter, Ferroelectric liquid crystal tunable filter, and Fabry Perot liquid crystal tunable filter.

29. The system of claim 13 further comprising an interferometer.

30. The system of claim 29 wherein the interferometer is selected from the group consisting of: Sagnac interferometers, Michelson interferometers, Twynam-Green interferometers, and Mach-Zehnder interferometers.

31. The system of claim 13 further comprising a fixed bandpass or a fixed band reject filter.

32. The system of claim 13 further comprising a polarizing filter.

* * * * *